(12) United States Patent
Moroz

(10) Patent No.: US 7,217,686 B1
(45) Date of Patent: May 15, 2007

(54) DNA SEQUENCE ENCODING ONCOFETAL FERRITIN PROTEIN

(75) Inventor: Chaya Moroz, Tel-Aviv (IL)

(73) Assignee: Gardino Investment N.V., Curacao (AN)

( * ) Notice: Subject to any disclaimer, the term of this patent is extended or adjusted under 35 U.S.C. 154(b) by 0 days.

(21) Appl. No.: 09/786,867

(22) PCT Filed: Sep. 8, 1999

(86) PCT No.: PCT/IL99/00485

§ 371 (c)(1),
(2), (4) Date: Aug. 21, 2001

(87) PCT Pub. No.: WO00/15788

PCT Pub. Date: Mar. 23, 2000

(51) Int. Cl.
*A61K 38/00* (2006.01)

(52) U.S. Cl. .......................... 514/2; 530/300; 536/23.1; 435/69.1; 435/70.1; 435/320.1

(58) Field of Classification Search .................... 514/2; 530/350; 536/23.1; 435/320.1, 69.1
See application file for complete search history.

(56) References Cited

U.S. PATENT DOCUMENTS

| | | | |
|---|---|---|---|
| 4,882,270 A | 11/1989 | Moroz | |
| 4,954,434 A | 9/1990 | Moroz | |
| 5,120,640 A | 6/1992 | Moroz et al. | |
| 5,283,177 A | 2/1994 | Moroz et al. | |
| 5,571,678 A | 11/1996 | Moroz et al. | |

FOREIGN PATENT DOCUMENTS

| | | |
|---|---|---|
| EP | 0 426 458 A2 | 5/1991 |
| WO | WO 89/09936 | 10/1989 |

OTHER PUBLICATIONS

Moroz et al., (J. Biol. Chem., vol. 277, Issue 15, 12901-12905, Apr. 12, 2002).*
Forre et al (2000, Scand J Rheumatol vol. 29, pp. 73-84).*
Friedmann (Scientific American, Jun. 1997, pp. 96-101).*
Verma and Somia (1997, Nature, vol. 389, pp. 239-242).*
Rubanyi (2001, Molecular Aspects of Medicine 22, pp. 113-142).*
Abstract—XP-002131126—Anderson et al. "Sequence and organization of the human mitochondrial genome", *Nature*, 290:457-465 (1981).
Abstract—XP-002131125—ZH Life Technology Kenkyusho "Human monocyte growth factor", p. 1, line 19-25 (1995).
Abstract of Japan—Manabu "Recombined growth factor for human monocyte, and DNA sequence coding the same" (1995).
XP-000877132—Fisch et al., "Placental isoferritin as a marker of early abortion in pregnancies induced by *in vitro* fertilization", *Piacenta*, 17:247-251 (1996).
XP-000876880—Rosen "Placental isoferritin-associated p43 in pregnancy and breast cancer minireview", *Neoplasma*, 43:357-362 (1996).

(Continued)

*Primary Examiner*—Misook Yu
(74) *Attorney, Agent, or Firm*—Browdy and Neimark, PLLC

(57) ABSTRACT

A DNA sequence coding for oncofetal ferritin 1 (OFF1) as well as an amino acid sequence encoded by the DNA sequence. Pharmaceutical compositions may be prepared comprising the above-sequences for treating various diseases, for facilitating transplantations and for treating pathological pregnancies.

8 Claims, 15 Drawing Sheets

```
5"
TTGACACCAG  ACCAACTGGT  AATGGTAGCG  ACCGGCGCTC  AGCTGGAATT  CCAAAAATG
TAATGCACAC  TCCATTGCAT  TCAGCCCGCC  TCTCCTTAGT  CGCCGCCATG  ACGACCGCGT
CCACCTCGCA  GGTGCGCCAG  AACTACCACC  AGGACTCAGA  GGCCGCCATC  AACCGCCAGA
TCAACCTGGA  GCTCTACGCC  TCCTACGTTT  ACCTGTCCAT  GTCTTACTAC  TTTGACCGCG
ATGATGTGGC  TTTGAAGAAC  TTTGCCAAAT  ACTTTCTTCA  CCAATCTCAT  GAGGAGAGGG
AACATGCTGA  GAAACTGATG  AAGCTGCAGA  ACCAACGAGG  TGGCCGAATC  TTCCTTCAGG
ATATCAAGAA  ACCAGACTGT  GATGACTGGG  AGAGCGGGCT  GAATGCAATG  GAGTGTGCAT
TACATTTGGA  AAAAAATGTG  AATCAGTCAC  TACTGGAATT  CCCTTCTCCT  ATCTCTCCCA
GTCCTAGCTG  CTGGCATCAC  TATACTACTA  ACAGACCGCA  ACCTCAACAC  CACCTTCTTC
GACCCCGCCG  GAGGAAGAGA  CCCCATTCTA  TACCAACACC  TATTCTGATT  TTTCGGTCAC
CCTGAAGTTT  ATATTCTTAT  CCTACCAGGC  TTCGGAATAA  TCTCCCATAT  TGTAACTTAC
TACTCCGGAA  ATCGCTGTCG  CCTAACCGCT  AACATTACTG  CAGGCCACCT  ACTCATGCAC
CTAATTGGAA  GCGCCACCCT  AGCAATATCA  ACCATTAACC  TTCCCTCTAC  ACTTATCATC
TTCACAATTC  TAATTCTACT  GACTATCCTA  GAAATCGCTG  TCGCCTTAAT  CCAAGCCTAC
GTTTTCACAC  TTCTAGTAAG  CCTCTACCTG  CACGACAACA  CATAAAAAAA  A        3"
```

OTHER PUBLICATIONS

XP-000877134—"Placental isoferritin: a new biomarker from conception to delivery", *British Journal of Obstetrics and Gynaecology*, 103:301-305 (1996).

XP-000876882—Yaniv et al., "p43, a new placental isoferritin subunit, is a growth factor for granulocyte-monocyte progenitor cells", p. 272.

XP-002131123—Moroz et al., "T-cell mitogenesis stimulates the synthesis of a mRNA species coding for a 43-kDa peptide reactive with CM-H-9, a monoclonal antibody specific for placental isoferritin", *Proc. Natl. Acad. Sci. USA*, 86:3282-3285 (1989).

XP-000876978—Garty et al., "High serum levels of placental isoferritin p43 component in down syndrome", *Human Sciences Press, Inc.*, 39-41 (1998).

XP-000876881—Higgy et al., "Differential expression of human ferritin H chain gene in immortal human breast epithelial MCF-10F cells", *Molecular Carcinogenesis*, 20:332-339 (1997).

XP-000876843—Boyd et al., "Structural and functional relationships of human ferritin H and L chains deduced from cDNA clones", *The Journal of Biological Chemistry*, 260:11755-11761 (1985).

Ferguson et al., "Comparison of a novel assay for breast cancer mucin to CA15-3 and carcinoembryonic antigen", *Journal of Clinical Oncology*, 10:1057-1065 (1992).

Werner et al., "Clinical utility and validation of emerging biochemical markers for mammary adenocarcinoma", *Clinical Chemistry*, 39:11(B)2386-2396 (1993).

Jones et al., "An Immunoradiometric assay for the acidic ferritin of human heart: application to human tissues, cells and serum", *Clinica Chimica Acta.*, 85:81-88 (1978).

Giannoulis et al., "Diagnostic value of serum ferritin in primary hepatocellular carcinoma", *Digestion*, 30:236-241 (1984).

Fine et al., "Ferritinaemia in cancer", *Nature*, 265:755-756 (1977).

Covell et al., "Isoferritins in plasma", 49-65 (1984).

Drysdale "Ferritin phenotypes: structure and metabolism", 41-67.

Brown et al., "Characterization and localization of human placental ferritin", 182:763-769 (1979).

Parhami-Seren et al., "A unique subunit structure of human placenta ferritin identified by the use of monoclonal antibodies", *G. I. Pat. Clin.*, 1:17-23 (1986).

Arosio et al., "On ferritin heterogeneity further evidence for heteropolymers", *The Journal of biological Chemistry*, 253:4451-4458 (1978).

Drysdale et al., "Carcinofetal human isoferritins in placenta and HeLa cells", *Cancer Research*, 34:3352-3354 (1974).

Matzner et al., "Serum ferritin in hematologic malignancies", *American Journal of Hematology*, 9:13-22 (1980).

Bezwoda et al., "Serum ferritin and Hodgkin's disease", *Scand J Haematol.*, 35:505-510 (1985).

Cragg et al., "Isoferritins in acute leukaemia", *Br. J. Cancer*, 35:635-642 (1977).

Halliday et al., "Isoferritin composition of tissues and serum in human cancer", *Cancer Research*, 36:4486-4490 (1976).

Jones et al., "Serum ferritin in patients with cancer: determinatin with antibodies to HeLa cell and spleen ferritin", *Clinica Chimica Acta*, 106:203-214 (1980).

Daly et al., "Comparison of a novel assay for breast cancer mucin to CA15-3 and carcinoembryonic antigen", *Journal of Clinical Oncology*, 10:1057-1065 (1992).

Demers et al., "CA-549: A new tumor marker for patients with advanced breast cancer", *Journal of Clinical Laboratory Analysis*, 2:168-173 (1988).

Dnistrian et al., "Evaluation of CA M26, CA M29, CA 15-3 and CEA and circulating tumor markers in breast cancer patients", *Tumor Biol.*, 12:82-90 (1991).

\* cited by examiner

5"
| TTGACACCAG | ACCAACTGGT | AATGGTAGCG | ACCGGCGCTC | AGCTGGAATT | CCAAAAAATG |
| TAATGCACAC | TCCATTGCAT | TCAGCCCGCC | TCTCCTTAGT | CGCCGCCATG | ACGACCGCGT |
| CCACCTCGCA | GGTGCGCCAG | AACTACCACC | AGGACTCAGA | GGCCGCCATC | AACCGCCAGA |
| TCAACCTGGA | GCTCTACGCC | TCCTACGTTT | ACCTGTCCAT | GTCTTACTAC | TTTGACCGCG |
| ATGATGTGGC | TTTGAAGAAC | TTTGCCAAAT | ACTTTCTTCA | CCAATCTCAT | GAGGAGAGGG |
| AACATGCTGA | GAAACTGATG | AAGCTGCAGA | ACCAACGAGG | TGGCCGAATC | TTCCTTCAGG |
| ATATCAAGAA | ACCAGACTGT | GATGACTGGG | AGAGCGGGCT | GAATGCAATG | GAGTGTGCAT |
| TACATTTGGA | AAAAAATGTG | AATCAGTCAC | TACTGGAATT | CCCTTCTCCT | ATCTCTCCCA |
| GTCCTAGCTG | CTGGCATCAC | TATACTACTA | ACAGACCGCA | ACCTCAACAC | CACCTTCTTC |
| GACCCCGCCG | GAGGAAGAGA | CCCCATTCTA | TACCAACACC | TATTCTGATT | TTTCGGTCAC |
| CCTGAAGTTT | ATATTCTTAT | CCTACCAGGC | TTCGGAATAA | TCTCCCATAT | TGTAACTTAC |
| TACTCCGGAA | ATCGCTGTCG | CCTAACCGCT | AACATTACTG | CAGGCCACCT | ACTCATGCAC |
| CTAATTGGAA | GCGCCACCCT | AGCAATATCA | ACCATTAACC | TTCCCTCTAC | ACTTATCATC |
| TTCACAATTC | TAATTCTACT | GACTATCCTA | GAAATCGCTG | TCGCCTTAAT | CCAAGCCTAC |
| GTTTTCACAC | TTCTAGTAAG | CCTCTACCTG | CACGACAACA | CATAAAAAAA | A      3" |

FIG. 1

CLONE p47                                      GGGGGACGGAACCCGG
CGCTCGTTCCCCACCCCGGCCGGCCGCCCATAGCCAGCCCTCCGTCAC

CLONE T 16                 TTGACACC
CTCTTCACCGCACCCTCGGACTGCCCCAAGGCCCCCGCCGCCGCTCC
AGACCAACTGGTAATGGTAGCGACCGGCGCTCAGCTGGAATTCCAAAA

AGCGCCGCGCAGCCACCGCCGCCGCCGCCGCCTCTCCTTAGTCGCCGCC
AATGTAATGCACACTCCATTGCATTCAGCCCGCCTCTCCTTAGTCGCCGCC

| ATG | ACG | ACC | GCG | TCC | ACC | TCG | CAG | GTG | CGC | CAG |
| ATG | ACG | ACC | GCG | TCC | ACC | TCG | CAG | GTG | CGC | CAG |
| AAC | TAC | CAC | CAG | GAC | TCA | GAG | GCC | GCC | ATC | AAC |
| AAC | TAC | CAC | CAG | GAC | TCA | GAG | GCC | GCC | ATC | AAC |
| CGC | CAG | ATC | AAC | CTG | GAG | CTC | TAC | GCC | TCC | TAC |
| CGC | CAG | ATC | AAC | CTG | GAG | CTC | TAC | GCC | TCC | TAC |
| GTT | TAC | CTG | TCC | ATG | TCT | TAC | TAC | TTT | GAC | CGC |
| GTT | TAC | CTG | TCC | ATG | TCT | TAC | TAC | TTT | GAC | CGC |
| GAT | GAT | GTG | GCT | TTG | AAG | AAC | TTT | GCC | AAA | TAC |
| GAT | GAT | GTG | GCT | TTG | AAG | AAC | TTT | GCC | AAA | TAC |
| TTT | CTT | CAC | CAA | TCT | CAT | GAG | GAG | AGG | GAA | CAT |
| TTT | CTT | CAC | CAA | TCT | CAT | GAG | GAG | AGG | GAA | CAT |
| GCT | GAG | AAA | CTG | ATG | AAG | CTG | CAG | AAC | CAA | CGA |
| GCT | GAG | AAA | CTG | ATG | AAG | CTG | CAG | AAC | CAA | CGA |
| CGT | GGC | CGA | ATC | TTC | CTT | CAG | GAT | ATC | AAG | AAA |
| GGT | GGC | CGA | ATC | TTC | CTT | CAG | GAT | ATC | AAG | AAA |
| CCA | GAC | TGT | GAT | GAC | TGG | GAG | AGC | GGG | CTG | AAT |
| CCA | GAC | TGT | GAT | GAC | TGG | GAG | AGC | GGG | CTG | AAT |
| GCA | ATG | GAG | TGT | GCA | TTA | CAT | TTG | GAA | AAA | AAT |
| GCA | ATG | GAG | TGT | GCA | TTA | CAT | TTG | GAA | AAA | AAT |
| GTG | AAT | CAG | TCA | CTA | CTG | GAA | CTG | CAC | AAA | CTG |
| GTG | AAT | CAG | TCA | CTA | CTG | GAA | TTC | CCT | TCT | CCT |
| GCC | ACT | GAC | AAA | AAT | GAC | CCC | CAT | TTG | TGT | GAC |
| ATC | TCT | CCC | AGT | CCT | AGC | TGC | TGG | CAT | CAC | TAT |

FIG. 2A

| TTC | ATT | GAG | ACA | CAT | TAC | CTG | AAT | GAG | CAG | GTG |
|---|---|---|---|---|---|---|---|---|---|---|
| ACT | ACT | AAC | AGA | CCG | CAA | CCT | CAA | CAC | CAC | CTT |
| AAA | GCC | ATC | AAA | GAA | TTG | GGT | GAC | CAC | GTG | ACC |
| CTT | CGA | CCC | CGC | CGG | AGG | AAG | AGA | CCC | CAT | TCT |
| AAC | TTG | CGC | AAG | ATG | GGA | GCG | CCC | GAA | TCT | GGC |
| ATA | CCA | ACA | CCT | ATT | CTG | ATT | TTT | CGG | TCA | CCC |
| TTG | GCG | GAA | TAT | CTC | TTT | GAC | AAG | CAC | ACC | CTG |
| TGA | AGTTTATATTCTTATCCTACCAGGCTTCGGAATAATCTCCCATATT |

GGA GAC AGT GAT AAT GAA AGC TAA GCCTCGGGCTAATT
GTAACTTACTACTCCGGAAATCGCTGTCGCCTAACCGCTAACATTACTGC

TCCCATAGCCGTGGGGTGACTTCCCTGGTCACCAAGGCAGTGCATGCAT
AGGCCACCTACTCATGCACCTAATTGGAAGCGCCACCCTAGCAATATCA

GCATGTTGGGGTTTCCTTTACCTTTTCTATAAGTTGTACCAAAACATCCAC
ACCATTAACCTTCCCTCTACACTTATCATCTTCACAATTCTAATTCTACTG

TTAAGTTCTTTGATTTGTACCATTCCTTCAAATAAAGAAATTTGGTACCCA
ACTATCCTAGAAATCGCTGTCGCCTTAATCCAAGCCTACGTTTTCACACT

AAAAAAAA
TCTAGTAAGCCTCTACCTGCACGACAACACATAAAAAAAA

FIG. 2A-1

Homology with FTH 55-428

59-569=ORF

463 CTTCTCCTATCTCTCCCAGTCCTAGCTGCTGGCATCACTATACTACTAAC 512
6486 CTTCTCCTATCTCTCCCAGTCCTAGCTGCTGGCATCACTATACTACTAAC 6535

513 AGACCGCAACCTCAACACCACCTTCTTCGACCCCGCCGGAGGAAGAGACC 562
6536 AGACCGCAACCTCAACACCACCTTCTTCGACCCCGCCGGAGGA<u>G</u>GAGACC 6505

563 CCATTCTATACCAACACCTATTCTGATTTTTCGGTCACCCTGAAGTTTAT 612
6506 CCATTCTATACCAACACCTATTCTGATTTTTCGGTCACCCTGAAGTTTAT 6635

613 ATTCTTATCCTACCAGGCTTCGGAATAATCTCCCATATTGTAACTTACTA 662
6636 ATTCTTATCCTACCAGGCTTCGGAATAATCTCCCATATTGTAACTTACTA 6685

663 CTCCGGAAA 671
6686 CTCCGGAAA 6694

Fig. 3

| | | | | | — A — | — AAAAAATG |
|---|---|---|---|---|---|---|
| TTGACACCAG | ACCAACTGGT | AATGGTAGCG | ACCGGCGCTC | AGCTGGATT | GCTAAAATGT |
| TAATGCACAC | TCCATTGCAT | | | | | |
| AATGCACACT | CCATTGGCAT | TCAGCCCGCC | TCTCCTTAGT | CGCCGCCATG | ACGACCGCGT |
| CCACCTCGCA | GGTGCGCCAG | AACTACCACC | AGGACTCAGA | GGCCGCCATC | AACCGCCAGA |
| TCAACCTGGA | GCTCTACGCC | TCCTACGTTT | ACCTGTCCAT | GTCTTACTAC | TTTGACCGCG |
| ATGATGTGGC | TTTGAAGAAC | TTTGCCAAAT | ACTTTCTTCA | CCAATCTCAT | GAGGAGAGGG |
| AACATGCTGA | GAAACTGATG | AAGCTGCAGA | ACCAACGAGG | TGGCCGAATC | TTCCTTCAGG |
| ATATCAAGAA | ACCAGACTGT | GATGACTGGG | AGAGCGGGCT | GAATGCAATG | GAGTGTGCAT |
| TACATTTGGA | AAAAAATGTG | AATCAGTCAC | TACTGGAATT | CCCTTCTCCT | ATCTCTCCCA |
| GTCCTAGCTG | CTGGCATCAC | TATACTACTA | ACAGACCGCA | ACCTCAACAC | CACCTTCTTC |
| GACCCCGCCG | GAGGAAGAGA | CCCCATTCTA | TACCAACACC | TATTCTGATT | TTTCGGTCAC |
| CCTGAAGTTT | ATATTCTTAT | CCTACCAGGC | TTCGGAATAA | TCTCCCATAT | TGTAACTTAC |
| TACTCCGGAA | ATCGCTGTCG | CCTAACCGCT | AACATTACTG | CAGGCCACCT | ACTCATGCAC |
| CTAATTGGAA | GCGCCACCCT | AGCAATATCA | ACCATTAACC | TTCCCTCTAC | ACTTATCATC |
| TTCACAATTC | TAATTCTACT | GACTATCCTA | GAAATCGCTG | TCGCCTTAAT | CCAAGCCTAC |
| GTTTTCACAC | TTCTAGTAA | GCCTCTACCT | GCACGACAAC | ACATAAAAAA | AA |

Fig. 4

```
TTGACACCAGACCAACTGGTAATGGTAGCGACCGGCGCTCAGCTGGAATTCCAAAAAATGT
AATGCACACTCCATTGCATTCAGCCCGCCTCTCCTTAGTCGCCGCC
met  thr  thr  ala  ser  thr  ser  gln  val  arg  gln
ATG  ACG  ACC  GCG  TCC  ACC  TCG  CAG  GTG  CGC  CAG asn  tyr  his  gln  asp  ser  glu  ala  ala  ile  asn
AAC  TAC  CAC  CAG  GAC  TCA  GAG  GCC  GCC  ATC  AAC arg  gln  ile  asn  leu  glu  leu  tyr  ala  ser  tyr
CGC  CAG  ATC  AAC  CTG  GAG  CTC  TAC  GCC  TCC  TAC val  tyr  leu  ser  met  ser  tyr  tyr  phe  asp  arg
GTT  TAC  CTG  TCC  ATG  TCT  TAC  TAC  TTT  GAC  CGC asp  asp  val  ala  leu  lys  asn  phe  ala  lys  tyr
GAT  GAT  GTG  GCT  TTG  AAG  AAC  TTT  GCC  AAA  TAC phe  leu  his  gln  ser  his  glu  glu  arg  glu  his
TTT  CTT  CAC  CAA  TCT  CAT  GAG  GAG  AGG  GAA  CAT ala  glu  lys  leu  met  lys  leu  gln  asn  gln  arg
GCT  GAG  AAA  CTG  ATG  AAG  CTG  CAG  AAC  CAA  CGA gly  gly  arg  ile  phe  leu  gln  asp  ile  lys  lys
GGT  GGC  CGA  ATC  TTC  CTT  CAG  GAT  ATC  AAG  AAA pro  asp  cys  asp  asp  trp  glu  ser  gly  leu  asn
CCA  GAC  TGT  GAT  GAC  TGG  GAG  AGC  GGG  CTG  AAT ala  met  glu  cys  ala  leu  his  leu  glu  lys  asn
GCA  ATG  GAG  TGT  GCA  TTA  CAT  TTG  GAA  AAA  AAT val  asn  gln  ser  leu  leu  glu  phe  pro  ser  pro
GTG  AAT  CAG  TCA  CTA  CTG  GAA  TTC  CCT  TCT  CCT ile  ser  pro  ser  pro  ser  cys  trp  his  his  tyr
ATC  TCT  CCC  AGT  CCT  AGC  TGC  TGG  CAT  CAC  TAT thr  thr  asn  arg  pro  gln  pro  gln  his  his  leu
ACT  ACT  AAC  AGA  CCG  CAA  CCT  CAA  CAC  CAC  CTT leu  arg  pro  arg  arg  arg  lys  arg  pro  his  ser
CTT  CGA  CCC  CGC  CGG  AGG  AAG  AGA  CCC  CAT  TCT ile  pro  thr  pro  ile  leu  ile  phe  arg  ser  pro
ATA  CCA  ACA  CCT  ATT  CTG  ATT  TTT  CGG  TCA  CCC
TGA  AGTTTATATTCTTATCCTACCAGGCTTCGGAATAATCTCCCATATTGTAACTTAC
TACTCCGGAAATCGCTGTCGCCTAACCGCTAACATTACTGCAGGCCACCTACTCATGCAC
CTAATTGGAAGCGCCACCCTAGCAATATCAACCATTAACCTTCCCTCTACACTTATCATC
TTCACAATTCTAATTCTACTGACTATCCTAGAAATCGCTGTCGCCTTAATCCAAGCCTAC
GTTTTCACACTTGTAGTAAGCCTCTACCTGCACGACAACACATAAAAAAAA
```

FIG. 5

```
        1061                              BNC
   TTGACACCAG  ACCAACTGGT  AATGGTAGCG  ACCGGCGCTC  AGCTGGAATT  CCAAAAAATG
   NCS
   TAATGCACAC  TCCATTGCAT  TCAGCCCGCC  TCTCCTTAGT  CGCCGCCATG  ACGACCGCGT
                                          X1
   CCACCTCGCA  GGTGCGCCAG  AACTACCACC  AGGACTCAGA  GGCCGCCATG  AACCGCCAGA
                                                                        17
   TCAACCTGGA  GCTCTACGCC  TCCTACGTTT  ACCTGTCCAT  GTCTTACTAC  TTTGACCGCG
        17
   ATGATGTGGC  TTTGAAGAAC  TTTGCCAAAT  ACTTTCTTCA  CCAATCTCAT  GAGGAGAGGG

AACATGCTGA  GAAACTGATG  AAGCTGCAGA  ACCAACGAGG  TGGCCGAATC  TTCCTTCAGG
                                                       2.1
   ATATCAAGAA  ACCAGACTGT  GATGACTGGG  AGAGCGGGCT  GAATGCAATG  GAGTGTGCAT
                                         ECOF
   TACATTTGGA  AAAAAATGTG  AATCAGTCAC  TACTGGAATT  CCCTTCTCCT  ATCTCTCCCA

GTCCTAGCTG  CTGGCATCAC  TATACTACTA  ACAGACCGCA  ACCTCAACAC  CACCTTCTTC

GACCCCGCCG  GAGGAAGAGA  CCCCATTCTA  TACCAACACC  TATTCTGATT  TTTCGGTCAC

CCTGAAGTTT  ATATTCTTAT  CCTACCAGGC  TTCGGAATAA  TCTCCCATAT  TGTAACTTAC
                   SPF
   TACTCCGGAA  ATCGCTGTCG  CCTAACCGCT  AACATTACTG  CAGGCCACCT  ACTCATGCAC
                   728                                             767
   CTAATTGGAA  GCGCCACCCT  AGCAATATCA  ACCATTAACC  TTCCCTCTAC  ACTTATCATC
     767                              16
   TTCACAATTC  TAATTCTACT  GACTATCCTA  GAAATCGCTG  TCGCCTTAAT  CCAAGCCTAC

GTTTTCACAC  TTCTAGTAAG  CCTCTACCTG  CACGACAACA  CATAAAAAAA  A
```

FIG. 7

| | | | | | |
|---|---|---|---|---|---|
| TTGACACCAG | ACCAACTGGT | AATGGTAGCG | ACCGGCGCTC | AGCTGGAATT | CCAAAAAATG |
| TAATGCACAC | TCCATTGCAT | TCAGCCCGCC | TCTCCTTAGT | CGCCGCC[ATG] | ACGACCGCGT |
| CCACCTCGCA | GGTGCGCCAG | AACTACCACC | AGGACTCAGA | GGCCGCCATC | AACCGCCAGA |
| TCAACCTGGA | GCTCTACGCC | TCCTACGTTT | ACCTGTCCAT | GTCTTACTAC | TTTGACCGCG |
| ATGATGTGGC | TTTGAAGAAC | TTTGCCAAAT | ACTTTCTTCA | CCAATCTCAT | GAGGAGAGGG |
| AACATGCTGA | GAAACTGATG | AAG[CTGCAGA]*Pst1* | ACCAACGAGG | TGGCCGAATC | TTCCTTCAGG |
| ATATCAAGAA | ACCAGACTGT | GATGACTGGG | AGAGCGGGCT | GAATGCAATG | GAGTGTGCAT |
| TACATTTGGA | AAAAAATGTG | AATCAGTCAC | TAC[TGGAAT]T*ECOR1* | CCCTTCTCCT | ATCTCTCCCA |
| GTCCTAGCTG | CTGGCATCAC | TATACTACTA | ACAGACCGCA | ACCTCAACAC | CACCTTCTTC |
| GACCCCGCCG | GAGGAAGAGA | CCCCATTCTA | TACCAACACC | TATTCTGATT | TTTCGGTCAC |
| CC[TGA]AGTTT | ATATTCTTAT | CCTACCAGGC | TTCGGAATAA | TCTCCCATAT | TGTAACTTAC |
| TACTCCGGAA | ATCGCTGTCG | CCTAACCGCT | AACATTACTG | CAGGCCACCT | ACTCATGCAC |
| CTAATTGGAA | GCGCCACCCT | AGCAATATCA | ACCATTAACC | TTCCCTCTAC | ACTTATCATC |
| TTCACAATTC | TAATTCTACT | GACTATCCTA | GAAATCGCTG | TCGCCTTAAT | CCAAGCCTAC |
| GTTTTCACAC | TTCTAGTAAG | CCTCTACCTG | CACGACAACA | CATAAAAAAA | A |

FIG. 8

SEQUENCE LISTING

<160> NUMBER OF SEQ ID NOS: 36

<210> SEQ ID NO 1
<211> LENGTH: 891
<212> TYPE: DNA
<213> ORGANISM: Homo sapiens

<400> SEQUENCE: 1

```
ttgacaccag accaactggt aatggtagcg accggcgctc agctggaatt ccaaaaaatg      60
taatgcacac tccattgcat tcagcccgcc tctccttagt cgccgccatg acgaccgcgt     120
ccacctcgca ggtgcgccag aactaccacc aggactcaga ggccgccatc aaccgccaga     180
tcaacctgga gctctacgcc tcctacgttt acctgtccat gtcttactac tttgaccgcg     240
atgatgtggc tttgaagaac tttgccaaat actttcttca ccaatctcat gaggagaggg     300
aacatgctga gaaactgatg aagctgcaga accaacgagg tggccgaatc ttccttcagg     360
```

| | |
|---|---:|
| atatcaagaa accagactgt gatgactggg agagcgggct gaatgcaatg gagtgtgcat | 420 |
| tacatttgga aaaaaatgtg aatcagtcac tactggaatt cccttctcct atctctccca | 480 |
| gtcctagctg ctggcatcac tatactacta acagaccgca acctcaacac caccttcttc | 540 |
| gaccccgccg gaggaagaga ccccattcta taccaacacc tattctgatt tttcggtcac | 600 |
| cctgaagttt atattcttat cctaccaggc ttcggaataa tctcccatat tgtaacttac | 660 |
| tactccggaa atcgctgtcg cctaaccgct aacattactg caggccacct actcatgcac | 720 |
| ctaattggaa gcgccaccct agcaatatca accattaacc ttccctctac acttatcatc | 780 |
| ttcacaattc taattctact gactatccta gaaatcgctg tcgccttaat ccaagcctac | 840 |
| gttttcacac ttctagtaag cctctacctg cacgacaaca cataaaaaaa a | 891 |

```
<210> SEQ ID NO 2
<211> LENGTH: 885
<212> TYPE: DNA
<213> ORGANISM: Homo sapiens

<400> SEQUENCE: 2
```

| | |
|---|---:|
| ggggacgga acccggcgct cgttccccac cccggccggc cgcccatagc cagccctccg | 60 |
| tcacctcttc accgcaccct cggactgccc caaggccccc gccgccgctc cagcgccgcg | 120 |
| cagccaccgc cgccgccgcc gcctctcctt agtcgccgcc atgacgaccg cgtccacctc | 180 |
| gcaggtgcgc cagaactacc accaggactc agaggccgcc atcaaccgcc agatcaacct | 240 |
| ggagctctac gcctcctacg tttacctgtc catgtcttac tactttgacc gcgatgatgt | 300 |
| ggctttgaag aactttgcca atactttcct tcaccaatct catgaggaga gggaacatgc | 360 |
| tgagaaactg atgaagctgc agaaccaacg aggtggccga atcttccttc aggatatcaa | 420 |
| gaaaccagac tgtgatgact gggagagcgg gctgaatgca atggagtgtg cattacattt | 480 |
| ggaaaaaaat gtgaatcagt cactactgga actgcacaaa ctggccactg acaaaaatga | 540 |
| ccccccatttg tgtgacttca ttgagacaca ttacctgaat gagcaggtga agccatcaa | 600 |
| agaattgggt gaccacgtga ccaacttgcg caagatggga gcgccgaat ctggcttggc | 660 |
| ggaatatctc tttgacaagc acaccctggg agacagtgat aatgaaagct aagcctcggg | 720 |
| ctaatttccc atagccgtgg ggtgacttcc ctggtcacca aggcagtgca tgcatgcatg | 780 |
| ttggggtttc ctttaccttt tctataagtt gtaccaaaac atccacttaa gttctttgat | 840 |
| ttgtaccatt ccttcaaata aagaaatttg gtacccaaaa aaaaa | 885 |

```
<210> SEQ ID NO 3
<211> LENGTH: 209
<212> TYPE: DNA
<213> ORGANISM: Homo sapiens

<400> SEQUENCE: 3
```

| | |
|---|---:|
| cttctcctat ctctcccagt cctagctgct ggcatcacta tactactaac agaccgcaac | 60 |
| ctcaacacca ccttcttcga ccccgccgga ggaggagacc ccattctata ccaacaccta | 120 |
| ttctgatttt tcggtcaccc tgaagtttat attcttatcc taccaggctt cggaataatc | 180 |
| tcccatattg taacttacta ctccggaaa | 209 |

```
<210> SEQ ID NO 4
<211> LENGTH: 891
<212> TYPE: DNA
<213> ORGANISM: Homo sapiens

<400> SEQUENCE: 4
```

-continued

```
ttgacaccag accaactggt aatggtagcg accggcgctc agctgggatt cctaaaatgt      60
aatgcacact ccattggcat tcagcccgcc tctccttagt cgccgccatg acgaccgcgt     120
ccacctcgca ggtgcgccag aactaccacc aggactcaga ggccgccatc aaccgccaga     180
tcaacctgga gctctacgcc tcctacgttt acctgtccat gtcttactac tttgaccgcg     240
atgatgtggc tttgaagaac tttgccaaat actttcttca ccaatctcat gaggagaggg     300
aacatgctga gaaactgatg aagctgcaga accaacgagg tggccgaatc ttccttcagg     360
atatcaagaa accagactgt gatgactggg agagcgggct gaatgcaatg gagtgtgcat     420
tacatttgga aaaaaatgtg aatcagtcac tactggaatt cccttctcct atctctccca     480
gtcctagctg ctggcatcac tatactacta acagaccgca acctcaacac caccttcttc     540
gaccccgccg gaggaagaga ccccattcta taccaacacc tattctgatt tttcggtcac     600
cctgaagttt atattcttat cctaccaggc ttcggaataa tctcccatat tgtaacttac     660
tactccggaa atcgctgtcg cctaaccgct aacattactg caggccacct actcatgcac     720
ctaattggaa gcgccaccct agcaatatca accattaacc ttccctctac acttatcatc     780
ttcacaattc taattctact gactatccta gaaatcgctg tcgccttaat ccaagcctac     840
gttttcacac ttctagtaag cctctacctg cacgacaaca cataaaaaaa a              891
```

<210> SEQ ID NO 5
<211> LENGTH: 165
<212> TYPE: PRT
<213> ORGANISM: Homo sapiens

<400> SEQUENCE: 5

```
Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
            20                  25                  30

Tyr Val Tyr Leu Ser Met Ser Tyr Tyr Phe Asp Arg Asp Asp Val Ala
        35                  40                  45

Leu Lys Asn Phe Ala Lys Tyr Phe Leu His Gln Ser His Glu Glu Arg
    50                  55                  60

Glu His Ala Glu Lys Leu Met Lys Leu Gln Asn Gln Arg Gly Gly Arg
65                  70                  75                  80

Ile Phe Leu Gln Asp Ile Lys Lys Pro Asp Cys Asp Asp Trp Glu Ser
                85                  90                  95

Gly Leu Asn Ala Met Glu Cys Ala Leu His Leu Glu Lys Asn Val Asn
            100                 105                 110

Gln Ser Leu Leu Glu Phe Pro Ser Pro Ile Ser Pro Ser Pro Ser Cys
        115                 120                 125

Trp His His Tyr Thr Thr Asn Arg Pro Gln Pro Gln His His Leu Leu
    130                 135                 140

Arg Pro Arg Arg Lys Arg Pro His Ser Ile Pro Thr Pro Ile Leu
145                 150                 155                 160

Ile Phe Arg Ser Pro
                165
```

<210> SEQ ID NO 6
<211> LENGTH: 24
<212> TYPE: DNA
<213> ORGANISM: Homo sapiens

<400> SEQUENCE: 6

```
ggtggcgacg actcctggag cccg                                              24

<210> SEQ ID NO 7
<211> LENGTH: 24
<212> TYPE: DNA
<213> ORGANISM: Homo sapiens

<400> SEQUENCE: 7
ttgacaccag accaactggt aatg                                              24

<210> SEQ ID NO 8
<211> LENGTH: 27
<212> TYPE: DNA
<213> ORGANISM: Homo sapiens

<400> SEQUENCE: 8
gaccgcgatg atgtggcttt gaagaac                                           27

<210> SEQ ID NO 9
<211> LENGTH: 24
<212> TYPE: DNA
<213> ORGANISM: Homo sapiens

<400> SEQUENCE: 9
gataggatct ttagcgacag ccga                                              24

<210> SEQ ID NO 10
<211> LENGTH: 24
<212> TYPE: DNA
<213> ORGANISM: Homo sapiens

<400> SEQUENCE: 10
atggcggcct ctgagtcctg gtgg                                              24

<210> SEQ ID NO 11
<211> LENGTH: 24
<212> TYPE: DNA
<213> ORGANISM: Homo sapiens

<400> SEQUENCE: 11
cgggctgaat gcaatggagt gtgc                                              24

<210> SEQ ID NO 12
<211> LENGTH: 18
<212> TYPE: DNA
<213> ORGANISM: Homo sapiens

<400> SEQUENCE: 12 gaccccatt tgtgtgac                                                      18

<210> SEQ ID NO 13
<211> LENGTH: 19
<212> TYPE: DNA
<213> ORGANISM: Homo sapiens

<400> SEQUENCE: 13
cgacgactcc tggagcccg                                                    19

<210> SEQ ID NO 14
<211> LENGTH: 24
<212> TYPE: DNA
<213> ORGANISM: Homo sapiens
```

-continued

```
<400> SEQUENCE: 14
ttgacaccag accaactcgt aatg                                          24

<210> SEQ ID NO 15
<211> LENGTH: 24
<212> TYPE: DNA
<213> ORGANISM: Homo sapiens

<400> SEQUENCE: 15
agccgacagc gatttctagg atag                                          24

<210> SEQ ID NO 16
<211> LENGTH: 27
<212> TYPE: DNA
<213> ORGANISM: Homo sapiens

<400> SEQUENCE: 16
gttcttcaaa gccacatcat cgcggtc                                       27

<210> SEQ ID NO 17
<211> LENGTH: 28
<212> TYPE: DNA
<213> ORGANISM: Homo sapiens

<400> SEQUENCE: 17
gctttcatta tcactgtctc ccagggtg                                      28

<210> SEQ ID NO 18
<211> LENGTH: 24
<212> TYPE: DNA
<213> ORGANISM: Homo sapiens

<400> SEQUENCE: 18
cagacgttct tcgccgagag tcgt                                          24

<210> SEQ ID NO 19
<211> LENGTH: 27
<212> TYPE: DNA
<213> ORGANISM: Homo sapiens

<400> SEQUENCE: 19
cagacgttct tcgccgagag tcgtcgg                                       27

<210> SEQ ID NO 20
<211> LENGTH: 20
<212> TYPE: DNA
<213> ORGANISM: Homo sapiens

<400> SEQUENCE: 20
catttcgggg attcggggga                                               20

<210> SEQ ID NO 21
<211> LENGTH: 20
<212> TYPE: DNA
<213> ORGANISM: Homo sapiens

<400> SEQUENCE: 21
gggggacgga acccggcgct                                               20

<210> SEQ ID NO 22
<211> LENGTH: 21
<212> TYPE: DNA
<213> ORGANISM: Homo sapiens
```

-continued

```
<400> SEQUENCE: 22
ccctctacac ttatcatctt c                                              21

<210> SEQ ID NO 23
<211> LENGTH: 24
<212> TYPE: DNA
<213> ORGANISM: Homo sapiens

<400> SEQUENCE: 23
ctatcctaga aatcgctgtc ggct                                           24

<210> SEQ ID NO 24
<211> LENGTH: 24
<212> TYPE: DNA
<213> ORGANISM: Homo sapiens

<400> SEQUENCE: 24
gtcactactg gaattccctt ctcc                                           24

<210> SEQ ID NO 25
<211> LENGTH: 24
<212> TYPE: DNA
<213> ORGANISM: Homo sapiens

<400> SEQUENCE: 25
ggagaaggga attccagtag tgac                                           24

<210> SEQ ID NO 26
<211> LENGTH: 21
<212> TYPE: DNA
<213> ORGANISM: Homo sapiens

<400> SEQUENCE: 26
ggaaatcgct gtcgcctaac c                                              21

<210> SEQ ID NO 27
<211> LENGTH: 21
<212> TYPE: DNA
<213> ORGANISM: Homo sapiens

<400> SEQUENCE: 27
ggttaggcga cagcgatttc c                                              21

<210> SEQ ID NO 28
<211> LENGTH: 20
<212> TYPE: DNA
<213> ORGANISM: Homo sapiens

<400> SEQUENCE: 28
ggccacgcgt cgactagtac                                                20

<210> SEQ ID NO 29
<211> LENGTH: 20
<212> TYPE: DNA
<213> ORGANISM: Homo sapiens

<400> SEQUENCE: 29
gtaatgcaca ctccattggc                                                20

<210> SEQ ID NO 30
<211> LENGTH: 18
<212> TYPE: DNA
```

<213> ORGANISM: Homo sapiens

<400> SEQUENCE: 30
gtaatgcaca ctccattg                                                18

<210> SEQ ID NO 31
<211> LENGTH: 18
<212> TYPE: DNA
<213> ORGANISM: Homo sapiens

<400> SEQUENCE: 31
gcgctcagct ggaattcc                                                18

<210> SEQ ID NO 32
<211> LENGTH: 18
<212> TYPE: DNA
<213> ORGANISM: Homo sapiens

<400> SEQUENCE: 32
ggaattccag ctgagcgc                                                18

<210> SEQ ID NO 33
<211> LENGTH: 29
<212> TYPE: DNA
<213> ORGANISM: Homo sapiens

<400> SEQUENCE: 33
gtgggatccc catgacgacc gcgtccacc                                    29

<210> SEQ ID NO 34
<211> LENGTH: 27
<212> TYPE: DNA
<213> ORGANISM: Homo sapiens

<400> SEQUENCE: 34
gactcgagtt aagccgacag cgatttc                                      27

<210> SEQ ID NO 35
<211> LENGTH: 29
<212> TYPE: DNA
<213> ORGANISM: Homo sapiens

<400> SEQUENCE: 35
gactcgagtc agggtgaccg aaaaatcag                                    29

<210> SEQ ID NO 36
<211> LENGTH: 31
<212> TYPE: DNA
<213> ORGANISM: Homo sapiens

<400> SEQUENCE: 36
cccgctcgag tcagggtgac cgaaaaatca g                                 31

DNA SEQUENCE ENCODING ONCOFETAL FERRITIN PROTEIN

REFERENCE TO RELATED APPLICATIONS

The present application is the national stage under 35 U.S.C. 371 of international application PCT/IL99/00485, filed Sep. 8, 1999, which designated the United States, and which international application was published under PCT Article 21(2) in the English language.

FIELD OF THE INVENTION

This invention relates to novel DNA sequences, amino acid sequences coded by them, detection method using said DNA sequences and pharmaceutical composition.

BACKGROUND OF THE INVENTION

Iron is known to be an essential element of the makeup of every living organism, but may also become toxic at physiological pH values by virtue of its tending to oxidize, hydrolyze and precipitate as insoluble ferric oxide polymers. The protein ferritin, found in all living cells, is the body's means for ensuring that iron toxicity does not occur. Ferritin functions by storing iron in the cells in a soluble and readily available form. The iron stored in cells may then be mobilized whenever needed by the body, for example for erythropoiesis.

The name "ferritin" actually encompasses a number of individual isomeric forms which are characteristic of different tissue types. Each isoferritin has 24 subunits of two distinct types, being light subunits (L) and heavy subunits (H). These subunits differ in molecular weight, the light subunit being about 18 kDa, and the heavy subunit about 19–21 kDa. The isoferritins extracted from different tissues or organs typically exhibit different isoelectric points, with the isoelectric focusing pattern of human tissues forming a continuous spectrum: those tissues associated with high iron storage have ferritin at the basic end of the spectrum (e.g. spleen and liver), while iron poor tissues, (e.g. heart and placenta) and malignant cells have acidic ferritin. (Drysdale, J., *Ciba Found. Symp.*, 51:41, 1976). The difference in isoelectric point appears to be related to the different distribution of light and heavy subunits in each type. Specifically, heavy subunits-rich ferritin are relatively acidic, and light chain rich ferritin are relatively basic (Covell, et al., in *Ferritin and Isoferritins as Biochemical Markers*, p. 49–65, 1984, Elsevier). Current studies indicate that the H and L subunits are encoded by a complex group of genes.

A specific type of acidic isoferritin has been shown to be characteristic of neoplastic cells and placental cells (Drysdale and Singer, *Cancer Res.*, 34:3352, 1974). This protein is also known as oncofetal ferritin or placental isoferritin (PLF). Human placental ferritin has been shown to be composed predominantly of a single subunit type comigrating with a liver ferritin standard on SDS-PAGE (Brown et al., *Biochem. J.*, 182:763, 1979). However, an immunoradiometric assay performed with anti-human spleen ferritin has shown tissue specific antigenicity for PLF (Brown et al., supra). A three subunit structure has been revealed for PLF (Moroz et al., *G. I. Pat. Clin.*, 1:17–23, 1986). In addition to the L and H subunits characteristic of all ferritin, there is also a high molecular weight (43 kDa) subunit which appears to be unique for human placenta, and thus provides a potential site for identification of the placental isoferritin molecule as distinguished from any other type of ferritin.

Various ferritin isoforms have been isolated from normal and malignant tissues, the most acidic ones predominating in tumor and fetal tissues (Drysdale J., 1976, *Ciba Found. Symp.* 51:41; Arosio et al., *J. Biol. Chem.*, 253:4451, 1978). It has been suggested that the assay or acidic isoferritin in the serum may be of value in the diagnosis of malignancy (Hazard et al., *Nature*, 265:755, 1977). Elevated concentrations of serum ferritin were found in patients suffering from a variety of malignant diseases, including acute lymphocytic leukemia (ALL) (Matzner et al., *Am. J. Hematol.*, 9:13, 1980), hepatoma (Giannoulis, *Digestion*, 30:236, 1984) and recently Hodgkin's disease (Bezwoda et al., *Scand. J. Haematol.*, 35:505, 1985). In assays based on antibodies HeLa cell ferritin, Hazard and Drysdale found higher concentrations of ferritin in sera from patients with various tumors than in the same sera assayed by antibodies directed against normal liver ferritin (Hazard et al., supra). Others have failed to demonstrate a consistent pattern of isoferritins in tumor tissues (Cragg et al., *Br. J. Cancer*, 35:635, 1977; Halliday et al., *Cancer Res.*, 36:4486, 1976) or in sera obtained from patients with tumors (Jones et al., *Clin. Chim. Acta.*, 85:81, 1978; Jones et al., *Clin. Chim. Acta.*, 106:203, 1980).

Although publications concerning the existence of oncofetal ferritin or placental isoferritins have been evident at least since the year 1976, up until today the sequence of this protein and the gene encoding therefor were not known. This is probably due to the fact that the protein itself is hydrophobic and almost devoid of iron and as a consequence extremely sticky and not capable of sedimentation even by high speed centrifugation thus hindering its isolation and purification. In addition, the sequence of the gene coding for oncofetal ferritin could not be found in regular cDNA libraries, probably due to the fact that its expression in these libraries is extremely low. The protein is secreted only by the placenta during pregnancy or by cancer cells in malignant diseases such as lymphoproliferative disorders, breast cancer and in HIV infection.

Breast cancer is a malignant disease effecting different populations at a rate of one to every 9–13 of women. Early diagnosis of breast cancer is known to considerably improve the prognosis of the patient. Diagnosis of breast cancer is based today mainly on imagining techniques such as mamma graphs verified at times by biopsies. Blood-based assays of breast cancer have been reported in the literature, for example, biomarker such as CA 15.3 (Daly, L. et al., *Comparison of a novel assay for breast cancer mucin to and CA 54 15.3 carcinoembryonic antigen*, J. Clin. Oncol., 10:1057–65, 1992); the CA 549(2) marker (Dormers, I. J., et al., *CA 549; a new tumor marker for patients with advanced breast cancer* J. Clin. Lab. Anal., 2:168–73, 1988); and the marker CA M29 CEA (Duistrian, A. M. et al., *Evaluation of CA M26, CA M29, CA 15.3 and CEA as circulating tumor markers in breast cancer patients. Tumor Biol.*, 12:82–90, 1991). However these assays, reported in the scientific community have not gained, to date, clinical significance (Werner M., et al., *Clinical utility and validation of emerging biochemical markers from mammary adenocarcinoma*, Clin. Chem., 39/11(B):2386–96, 1993).

U.S. Pat. No. 4,882,270 discloses an assay for the detection of breast cancer based on determination of oncofetal ferritin. The assay is based on binding of the oncofetal ferritin to specific monoclonal antibodies.

Pathological pregnancy is a term commonly used to describe a multitude of symptoms which create difficulties in carrying a child to term and include spontaneous abortion and miscarriage, premature contractions, toxemia, premature delivery. U.S. Pat. No. 4,954,434 discloses the fact that low levels or absence of PLF in pregnant women can serve as a marker for potentially high risk pregnancy. Detection of this state is again achieved by monoclonal antibodies which has PLF specificity. This patent also concerns treatment and prevention of actual and potentially pathological pregnancy by the administration of this protein. However, since the sequence of the protein was not known at the date of the patents, the treatment suggested involved administration of partially purified protein and not of recombinant pure proteins.

U.S. Pat. Nos. 5,571,678, 5,120,640 and 5,283,177 are all directed to methods for assaying the presence and evaluating the prognosis of acquired immunodeficiency associated with HIV induction, by determining levels of placental isoferritin by monoclonal antibodies.

All the above detection methods concern antibody-based assays. While such assays are known to be useful in conditions where the level of the protein to be detected is quite high, they are notorious for eliciting a false-negative answer where the protein level is low. Against this, assays based on amplification of mRNA (RT-PCR) are much more sensitive and can detect even minute expression of mRNA. Thus there is need today for a RT-PCR method for detection of oncofetal ferritin for detection of breast cancer and for diagnosis of high risk pregnancies at its early stage.

Furthermore, it would have been desirable to provide pure oncofetal ferritin protein prepared by recombinant processes for therapeutic and vaccination purposes.

SUMMARY OF THE INVENTION

The present invention is based on the finding of the sequence of the oncofetal ferritin gene and of the oncofetal ferritin protein. The inventor was the first to discover the full sequence of the gene that codes for the protein termed hereinafter as "oncofetal ferritin 1 (OFF1) protein".

Thus, the present invention concerns a DNA sequence coding for the subunit of the oncofetal ferritin protein termed "oncofetal ferritin 1" (OFF1) protein selected from the group consisting of:

(i) a DNA sequence as depicted in FIG. 1;
(ii) a DNA sequence as depicted in FIG. 4;
(iii) a DNA sequence which codes for the same amino acid sequences encoded by the sequence of (i) or (ii);
(iv) fragments of any of the sequences of (i) to (iii) that code for a functionally equivalent gene product;
(v) a DNA sequence that has at least 80% homology, as determined by hybridization under stringent conditions, to any one of the sequences of (i) to (iv) and code for a physiologically active protein.
(vi) a DNA sequence that hybridizes to the sequences of (i) to (iv) under highly stringent conditions, e.g., hybridization to filter-bound DNA in 0.5M $NaHPO_4$, 7% sodium dodecyl sulfate (SDS), 1 mM EDTA at 65° C., and washing in 0.1×SSC/0.1% SDS at 68° C. (Ausubel F. M. et al. eds., 1989, *Current Protocols in Molecular Biology*, Vol. I, Green Publishing Assoc., Inc. and John Wiley & Sons, Inc. New York at p. 2.10.3), which can either be used as a probe for OFF1, or which encodes functionally equivalent gene product; and
(vii) a DNA sequence that hybridizes to the sequences of (i) to (iv) under moderately stringent conditions, e.g., washing in 0.2×SCC/0.1% SDS at 42° C. (Ausubel et al., 1989, supra), yet which still encodes a functionally equivalent gene product.

The sequence of FIG. 1 was isolated from a cDNA library obtained from breast cancer patients while the DNA sequence of FIG. 4 was obtained when using PCR amplification where the sequence of FIG. 1 was used as a template. The two sequences differ only in the 5' non-coding region which include 2 single nucleotide substitutions as well as a single base insertion and one deletion.

The DNA sequences of the invention also include DNA sequences which code for the same amino acid sequences as those of FIGS. 1 or 4. It is known that due to the degenerative nature of the genetic code, a large number of alternative DNA sequences, may code for the same proteins. Thus all sequences which code for the same amino acid sequences are encompassed by the scope of the invention.

The present invention further concerns DNA sequences having at least 80% homology either to the DNA sequence of FIG. 1 or 4, or to the DNA sequences coding the same types of amino acid sequences, the homology determined by hybridization under stringent conditions. Examples of highly stringent conditions are given in (vi) above and of moderately stringent conditions are given in (vii) above. The artesian will appreciate the fact that there exists a large number of sequences capable of hybridization under such conditions, some of which code for more physiologically active OFF1 proteins than others. Those sequences which fall under the scope of the invention, are those which code for a functionally equivalent gene product, as will be explained hereinbelow.

The present invention also encompasses DNA sequences that hybridize to the sequences of FIGS. 1 or 4, or to the cDNA inserts contained in the deposited cells, under highly stringent conditions, as specified above. Such DNAs can be used as probes to detect the OFF-1 gene or mRNAs (e.g. by hybridization or PCR amplification assays). Alternatively DNAs that hybridize under highly stringent or less stringent conditions (specified above), yet which encode a functionally equivalent gene product are also encompassed by the invention.

The present invention further concerns fragments of all the above sequences, which code for an OFF1 protein having functionally equivalent gene product will be explained hereinbelow.

The term "functionally equivalent gene product", refers to an amino acid sequence, which is physiologically active in a manner similar to that of the native OFF1 protein. Such an activity can be tested, for example, by determining the immunosuppressive activity in cell mediated immunity, as is well known in the art.

The present invention further concerns expression vectors comprising said DNA sequences, as well as a host cells transfected with such expression vectors. Expression may be obtained in any suitable pro- or eucaryotic expression systems using known methods e.g. as described in Genentech EP 200341.

Suitable expression vectors are DNA sequences encoding OFF1 and operably linked to suitable control sequences capable of effecting the expression of OFF1 in the host. Such control sequences include a transcriptional promoter, an optional operator sequence to control transcription, a sequence encoding suitable mRNA ribosomal binding sites, and sequences that control termination of transcription and translation. For expression of OFF1 in eukaryotic cells, the vector also should include DNA encoding a selection gene.

Vectors include plasmids, viruses (including phages) and integratable DNA fragments, i.e. fragments that are integratable into the host genom by recombination.

Preferred host cells are cells derived from multicellular organisms. In principle, any higher eucaryotic cell culture is workable whether from vertebrate or invertebrate culture. Examples useful in host cell lines are Chinese Hamster Ovary (CHO) cell lines and COS 7 cell lines.

In another embodiment of the present invention, the cells and tissues may be engineered to express an endogenous gene under the control of inducible regulatory elements, in which case the regulatory sequences of the endogenous gene may be replaced by homologous recombination. As described herein, gene targeting can be used to replace a gene's existing regulatory region with a regulatory sequence isolated from a different gene or a novel regulatory sequence synthesized by genetic engineering methods. Such regulatory sequences may be comprised of promoters, enhancers, scaffold-attachment regions, negative regulatory elements, transcriptional initiation sites, regulatory protein binding sites or combinations of said sequences. Alternatively, sequences which affect the structure or stability of the RNA or protein produced may be replaced, removed, added, or otherwise modified by targeting, including polyadenylation signals, mRNA stability elements, splice sites, leader sequences for enhancing or modifying transport or secretion properties of the protein, or other sequences which alter or improve the function or stability of protein or RNA molecules.

The targeting event may be a simple insertion of the regulatory sequence, placing the gene under the control of the new regulatory sequence, e.g., inserting a new promoter or enhancer or both upstream of a gene. Alternatively, the targeting event may be a simple deletion of a regulatory element, such as the deletion of a tissue-specific negative regulatory element. Alternatively, the targeting event may replace an existing element; for example, a tissue-specific enhancer can be replaced by an enhancer that has broader or different cell-type specificity than the naturally occurring elements. Here, the naturally occurring sequences are deleted and new sequences are added. In all cases, the identification of the targeting event may be facilitated by the use of one or more selectable marker genes that are contiguous with the targeting DNA, allowing for the selection of cells in which the exogenous DNA has integrated into the host cell genome. The identification of the targeting event may also be facilitated by the use of one or more marker genes exhibiting the property of negative selection, such that the negatively selectable marker is linked to the exogenous DNA, but configured such that the negatively selectable marker flanks the targeting sequence, and such that a correct homologous recombination event with sequences in the host cell genome does not result in the stable integration of the negatively selectable marker. Markers useful for this purpose include the Herpes simplex virus thymidine kinase (TK) gene or the bacterial xanthine-guanine phosphoribosyl-transferase (gpt) gene.

The gene targeting or gene activation techniques which can be used in accordance with this aspect of the invention are more particularly described in U.S. Pat. No. 5,272,071 to Chappel; U.S. Pat. No. 5,578,461 to Sherwin et al.; International Application No. PCT/US92/09627 (WO93/09222) by Selden et al.; and International Application No. PCT/US90/06436 (WO91/06667) by Skoultchi et al., each of which is incorporated by reference herein in its entirety.

The present invention of course concerns also a recombinant protein coded by the above DNA sequence. Said recombinant protein is in fact the first recombinant OFF-1 protein produced, and enables production of large amounts of such protein in a pure form for therapeutic and detection purposes as will be explained hereinbelow.

The present invention further concerns anti-sense RNA sequences, which are complementary to the mRNA sequences transcribed from the above DNA sequences, and thus are capable of neutralizing the expression of native OFF-1 gene in cells. The present invention further concerns DNA sequences coding for said anti-sense mRNA, as well as expression vectors comprising said DNA sequences.

The present invention also concerns pharmaceutical compositions of two types.

According to the first aspect of the invention, termed "the OFF1 activating aspect" the pharmaceutical compositions of the invention comprise DNA sequences coding for the OFF1 protein, expression vectors comprising said DNA sequences, for expression in specific target cells, or the recombinant OFF1 protein itself. The above agents may be used in the immunization of a subject against diseases which are manifested by abnormally high expression of the OFF1. Examples of such diseases are: cancer, in general, and breast cancer and lymphomas in particular as well as HIV infections.

The pharmaceutical composition according to the activating aspect of the invention may be used, as such, for increasing the level of the OFF1 protein for the treatment of conditions manifested by lower than normal levels of the OFF1 protein. If the level of the OFF1 protein can be raised again to normal level, either by administering to the subject recombinant OFF1 protein, or by transfecting the subject's target cells with an expression vector comprising the DNA coding for the OFF1 protein, then the pathological conditions may be alleviated. Pathological conditions treated by these pharmaceutical compositions are pathological pregnancies manifested by spontaneous abortion and miscarriage, premature contractions, toxemia and premature delivery. In addition, the pharmaceutical compositions may be used to inhibit transplant rejection, for example, specific T-cell mediated immunity like that of a mother against her embryo.

Using the same principal, the pharmaceutical compositions of the invention may also be used for the treatment, alleviation, or prevention of autoimmune diseases, such as: Coeliac disease, Rheumatoid arthritis, and Multiple Sclerosis which are T-cell mediated autoimmune diseases.

By another option, the pharmaceutical composition of the activation aspect of the invention may be used to support normal pregnancies, for example, for increasing the chances of success of in vitro fertilization (IVF), in both human and non human subjects.

According to another surprising finding it was found that OFF1 can serve as a growth factor for bone marrow progenitor cells. Thus the pharmaceutical composition of the invention may be used to enhance growth of bone marrow progenitor cells, for example, where due to some pathological condition their number has decreased. Such a condition occurs, for example, in patients treated by mega doses of cytotoxic drugs which kill bone marrow cells such as cancer patients, HIV infected patients and the like. In addition the pharmaceutical compositions of the invention could be used in patients who need bone marrow replacements such as those with genetic metabolic defects or autoimmune diseases.

By another alternative the DNA coding for OFF1 can be used in the development of a chimera which will enable further grafting of organ allografts or xenografts identical with the bone marrow donor.

In addition, a preparation comprising OFF1 can be used ex vivo as a growth factor for bone marrow progenitor cells, for example, from bone marrow obtained from a donor prior to implantation.

An example of bone marrow progenitor cells are granulocyte monocyte progenitor cells.

By another aspect of the invention, termed "the OFF-1 neutralizing aspect" the pharmaceutical compositions of the invention comprise anti-sense mRNA to the OFF-1, expression vectors comprising DNA sequences coding for said anti-sense mRNA, or antibodies against the OFF-1 protein. The neutralizing aspect of the invention, is intended to lower the levels of OFF-1, where it is abnormally high as compared to normal tissue, notably for the treatment of cancer, especially breast cancer.

By another option the neutralizing aspect of the invention may be used in order to reduce the normal level of OFF1 which is required to maintain a pregnancy to term and thus cause abortion (Moroz, C., 9$^{th}$ International Congress of Immunology, San Francisco, 1995).

The present invention further concerns a method for the detection of cancer, or for the evaluation of the prognosis of a cancer patient, by determining the level of the OFF1 gene expression in said patients.

U.S. Pat. No. 4,882,270 discloses a method for detecting breast cancer, by using antibodies against isoferritin placental protein.

This method detects said protein in early stages of the cancer only on lymphocytes not in the serum. The protein can be detected in the serum only at a very late stage of the disease when the tumor has already metastasized. The problem with lymphocyte-based detection, is double fold: first, technical issues concerning detection are quite severe, since there is a requirement to isolate fresh lymphocytes from the blood and assay within hours without an opportunity to retest at a later date. This severe technical problem prohibits the use of this method of detection in widely used screening assays. Second, during progressive stages of cancer, the number of positive lymphocytes decreases dramatically, and thus it is not possible to detect the cancer, using lymphocytes directed anti-ferritin antibodies. Thus, according to said U.S. patent, it is possible to detect cancer at its early stage, where the number of lymphocytes is high, as well as at the very last stages, where the level of the isoferrin placental protein is so high that it is shed to the serum, but in most stages of the cancer, the low number of positive lymphocytes avoids detection of cancer.

Against this, the detection methods of the present invention, are based on RNA amplification, and are sensitive enough to detect even slightly elevated levels of the OFF1 mRNA present in small amounts of the patient's blood in virtually all stages of cancer. The method of the invention detects the mRNA in circulating cancer cells, whereas the protein is shed from tumors and binds to lymphocytes.

In addition to detection of the presence of cancer, the level of OFF1 protein is also a good indicator of the prognosis of cancer, for example the change in mRNA level after removal of the tumor by surgery or chemotherapy may indicate disease prognosis.

Examples of cancers which can be detected by the methods of the invention are breast cancer, hepotomas, leukemias, lymphomas and embryonal tumors such as neuroblastoma and hepatoblastoma.

In addition, elevated levels of OFF1 expression, are typical of Down Syndrome. In Down Syndrome there are elevations of embryonal proteins like α-fetoprotein (AFP). Also the Syndrome is associated with decreased immunoreactivity and high incidence of cancer. Thus by detecting high levels of this protein it is possible to determine also Down's disease.

By another embodiment, the present invention concerns a method for the detection of diseases connected with pathological pregnancies, comprising detecting a lower level than normal of the OFF-1 expression. The term "pathological pregnancies" groups together a large number of disorders including spontaneous abortion and miscarriage, premature contractions, toxemia, premature delivery.

The detection of the level of the OFF-1 expression, both for determining higher than normal levels (various types of cancer) or lower than normal levels (various types of pathological pregnancies) can be carried out by utilizing reverse transcriptase polymerized chain reaction (RT-PCR). This method, considerably amplifies the OFF-1 mRNA present in the blood enabling its detection, even in minute levels.

The present invention further concerns a method for the isolation of the cDNA of the invention as specified in FIG. 1 or 4 as will be appreciated in the "Detailed Description" section of the specification.

The present invention further concerns primers for use in the above isolation method. These primers may also be used in RT-PCR, for the detection purposes of the invention. The primers are selected from the group consisting of:

```
5' GGT GGC GAC GAC TCC TGG AGC CCG 3'              SEQ ID NO:6

5' TTG ACA CCA GAC CAA CTG GTA ATG 3'              SEQ ID NO:7

5' GAC CGC GAT GAT GTG GCT TTG AAG AAC 3'          SEQ ID NO:8

5' GAT AGG ATC TTT AGC GAC AGC CGA 3'              SEQ ID NO:9

5' ATG GCG GCC TCT GAG TCC TGG TGG 3'              SEQ ID NO:10

5' CGG GCT GAA TGC AAT GGA GTG TGC 3'              SEQ ID NO:11

5' GAC CCC CAT TTG TGT GAC 3'                      SEQ ID NO:12

5' CGA CGA CTC CTG GAG CCC G 3'                    SEQ ID NO:13

5' Biotin-TTG ACA CCA GAC CAA CTC GTA ATG 3'       SEQ ID NO:14

5' AGC CGA CAG CGA TTT CTA GGA TAG 3'              SEQ ID NO:15

5' GTT CTT CAA AGC CAC ATC ATC GCG GTC 3'          SEQ ID NO:16
```

-continued

| | |
|---|---|
| 5' GCT TTC ATT ATC ACT GTC TCC CAG GGT G 3' | SEQ ID NO:17 |
| 5' CAG ACG TTC TTC GCC GAG AGT CGT 3' | SEQ ID NO:18 |
| 5' CAG ACG TTC TTC GCC GAG AGT CGT CGG 3' | SEQ ID NO:19 |
| 5' CAT TTC GGG GAT TCG GGG GA 3' | SEQ ID NO:20 |
| 5' GGG GGA CGG AAC CCG GCG CT 3' | SEQ ID NO:21 |
| 5' CCC TCT ACA CTT ATC ATC TTC 3' | SEQ ID NO:22 |
| 5' CTA TCC TAG AAA TCG CTG TCG GCT 3' | SEQ ID NO:23 |
| 5' GTC ACT ACT GGA ATT CCC TTC TCC 3' | SEQ ID NO:24 |
| 5' GGA GAA GGG AAT TCC AGT AGT GAC 3' | SEQ ID NO:25 |
| 5' GGA AAT CGC TGT CGC CTA ACC 3' | SEQ ID NO:26 |
| 5' GGT TAG CGC ACA GCG ATT TCC 3' | SEQ ID NO:27 |
| 5' GGC CAC GCG TCG ACT AGT AC 3' | SEQ ID NO:28 |
| 5' GTA ATG CAC ACTCCA TTG GC 3' | SEQ ID NO:29 |
| 5' GTA ATG CAC ACT CCA TTG 3' | SEQ ID NO:30 |
| 5' GCG CTC AGC TGG AAT TCC 3' | SEQ ID NO:31 |
| 5' GGA ATT CCA GCT GAG CGC 3' | SEQ ID NO:32 |
| 5' GTG GGA TCC CCA TGA CGA CCG CGT CCA CC 3' | SEQ ID NO:33 |
| 5' GAC TCG AGT TAA GCC GAC AGC GAT TTC 3' | SEQ ID NO:34 |
| 5' GAC TCG AGT CAG GGT GAC CGA AAA ATC AG 3' | SEQ ID NO:35 |
| 5' CCC GCT CGA GTC AGG GTG ACC GAA AAA TCA G 3' | SEQ ID NO:36 |

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 1 shows the nucleic acid sequence (SEQ ID NO:1) of clone T16 isolated from T47D breast cancer cDNA library. Initiation and termination codons of the open reading frame are indicated by dark bars;

FIG. 2A shows a comparison of the nucleic acid sequences (upper sequence) (SEQ ID NO:2) of clone 4.7 isolated from a placenta cDNA library exhibiting normal human FTH, and the sequences (lower sequence) of clone T16 (SEQ ID NO:1) isolated from human breast cancer T47D cDNA library. Initiation and termination codons of the open reading frame are marked by dark boxes;

FIG. 3 shows a comparison of sequence homology between cDNA clone T16 (residues 463–671 of SEQ ID NO:1) and human mitochondrial cytochrome oxidase I DNA (SEQ ID NO:3);

FIG. 4 shows a comparison of nucleic acid sequences between placental cDNA obtained by PCR amplification using T16 specific primers (upper sequence) (residues 24–822 of SEQ ID NO:1) and T16 cDNA sequence obtained from the T16 cDNA clone (lower sequence) (SEQ ID NO:4). Identical nucleic acid sequences are indicated by a dotted line. Initiation and termination codons are indicated by a dark bar;

FIG. 5 shows the nucleic acid sequence and deduced amino acid sequence (SEQ ID NO:5) of the cDNA of OFF1;

FIG. 7 shows the sequence of clone T16 (SEQ ID NO:1). Primers used for PCR are indicated in the above sequence;

FIG. 8 shows the restriction enzyme map sequence of clone T16 (SEQ ID NO:1);

DETAILED DESCRIPTION OF THE INVENTION

EXPERIMENTAL PROCEDURES

EXAMPLE 1

Cloning of OFF1 cDNA

Figure 2B:
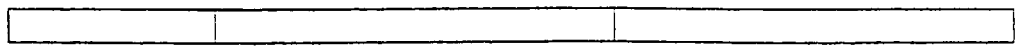
FIG. 2B shows in a schematic representation the comparison of the two sequences shown in FIG. 2A. Differences in nucleic acid sequences are represented by the shaded areas.

λgt11 cDNA libraries were prepared using total poly A+RNA from human breast cancer cell line T47D or from human placenta. Both libraries were randomly primed from total poly (A)+RNA. EcoRI linkers were attached to the cDNAs which were inserted into the EcoRI site of the bacteriophage λgt11.

About 10⁶ plaque forming units were screened by using human liver ferritin (FTH) cDNA provided by R. Cortese (Constanzo et al., *EMBO*, 3:23–27, 1984). Plaque hybridization was carried out according to Berton, W. D. and Davis R. W., (*Screening λgt recombinant clones by hybridization to single plaques in-site, Science*, 196:180–182 (1997)). In brief, plaque hybridization was carried out at 42° C., 5×SSC and subsequent washing 3 times with 2×SSC 0.1% SDS at room temperature and twice with 1×SSC, 0.1% SDS at 68° C.

Clones were isolated that gave hybridization signals after two rounds of screening. PCR amplification was performed on clones using one primer from the λgt11 vector (λgt11 F-1060 or λgt11 R-1061, Table 1) and one FTH gene-specific primer (either 17R to amplify toward the 5' end of 17F to amplify toward the 3' end; as indicated in Table 1) as described above, PCR amplification was performed for 30 cycles under standard conditions. PCR products from the clones derived from both the 5' and the 3' end of the cDNA clone were selected according to their size, so that their sequence would produce a contig of maximum length. PCR products were purified by Qiagen PCR purification columns according to the manufacturer's instructions and were sequenced using standard protocols for the ABI373 or 377 primers mated sequencer with the 1060 and 1061 primers (Table 1) and specific primers until the full sequence was determined.

TABLE 1

List of Primers

| Name | #MR | Sequence | SEQ ID NO: | | |
|---|---|---|---|---|---|
| 1060F | 24 | 5' GGT GGC GAC GAC TCC TGG AGC CCG 3' | 6 | 75% | |
| 1061R | 24 | 5' TTG ACA CCA GAC CAA CTG GTA ATG 3' | 7 | 45.80% | |
| 17F | 27 | 5' GAC CGC GAT GAT GTG GCT TTG AAG AAC 3' | 8 | 52% | 27618 |
| X1.1F | 24 | 5' GAT AGG ATC TTT AGC GAC AGC CGA 3' | 9 | 50% | 24880 |
| X.1.1R | 24 | 5' ATG GCG GCC TCT GAG TCC TGG TGG 3' | 10 | 67% | |
| 2.1F | 24 | 5' CGG GCT GAA TGC AAT GGA GTG TGC 3' | 11 | 58% | |
| 3.4F | 18 | 5' GAC CCC CAT TTG TGT GAC 3' | 12 | 55.50% | |
| 1060F/S | 19 | 5' CGA CGA CTC CTG GAG CCC G 3' | 13 | 73.70% | |
| 1061r/Bio | 24 | 5' Biotin-TTG ACA CCA GAC CAA CTC GTA ATG 3' | 14 | 45.80% | |
| 16X.1R | 24 | 5' AGC CGA CAG CGA TTT CTA GGA TAG 3' | 15 | 50% | 24879 |
| 17R | 27 | 5' GTT CTT CAA AGC CAC ATC ATC GCG GTC 3' | 16 | 52% | 27385 |
| 3'COD R | 28 | 5' GCT TTC ATT ATC ACT GTC TCC CAG GGT G 3' | 17 | 50% | 28313 |
| 5' NCF | 24 | 5' CAG ACG TTC TTC GCC GAG AGT CGT 3' | 18 | 58% | 24870 |
| 4869 | 27 | 5' CAG ACG TTC TTC GCC GAG AGT CGT CGG 3' | 19 | 63% | |
| NFG | 20 | 5' CAT TTC GGG GAT TCG GGG GA 3' | 20 | 60% | |
| NFGP-2 | 20 | 5' GGG GGA CGG AAC CCG GCG CT 3' | 21 | 80% | 201880 |
| 767-F | 21 | 5' CCC TCT ACA CTT ATC ATC TTC 3' | 22 | 43% | 211616 |
| 16-F | 24 | 5' CTA TCC TAG AAA TCG CTG TCG GCT 3' | 23 | 50% | 241173 |
| ECO-F | 24 | 5' GTC ACT ACT GGA ATT CCC TTC TCC 3' | 24 | 50% | 24960 |
| ECO-R | 24 | 5' GGA GAA GGG AAT TCC AGT AGT GAC 3' | 25 | 50% | 24961 |
| SPF | 21 | 5' GGA AAT CGC TGT CGC CTA ACC 3' | 26 | 57% | 211667 |
| SPR | 21 | 5' GGT TAG CGC ACA GCG ATT TCC 3' | 27 | 57% | 211668 |
| AUAP | 20 | 5' GGC CAC GCG TCG ACT AGT AC 3' | 28 | 65% | 202738 |
| NC-F | 20 | 5' GTA ATG CAC ACTCCA TTG GC 3' | 29 | 50% | 203814 |
| SNC-F | 18 | 5' GTA ATG CAC ACT CCA TTG 3' | 30 | 44% | 181897 |
| BNC-F | 18 | 5' GCG CTC AGC TGG AAT TCC 3' | 31 | 55.50% | 181898 |
| BNC-R | 18 | 5' GGA ATT CCA GCT GAG CGC 3' | 32 | 61.10% | 181905 |
| pGEX-F | 29 | 5' GTG GGA TCC CCA TGA CGA CCG CGT CCA CC3' | 33 | 67% | 29391 |
| pGEX-R1 | 27 | 5' GAC TCG AGT TAA GCC GAC AGC GAT TTC 3' | 34 | 51.85% | 27578 |
| pGEX-R2 | 29 | 5' GAC TCG AGT CAG GGT GAC CGA AAA ATC AG 3' | 35 | 51.70% | 29396 |
| pGEX-R3 | 31 | 5' CCCGCTCGAGTCAGGGTGACCGAAAAATCAG 3' | 36 | 58% | 31277 |

EXAMPLE 2

Sequence Analysis

The cDNA sequences and its deduced protein sequence were used to search the complete combined Gene Bank/EMBL database and the complete Swiss Prot database with BLAST and FASTA programs, respectively.

EXAMPLE 3

RNA Preparation and Northern Blot Analysis

Total RNA was extracted from cells by guanidinium isothiocyanate solubilization and prepared by phenol-chloroform extraction. PolyA+ RNA was purified using 2 rounds of oligo(dT) chromatography. Total RNA (25 μg) was separated by electrophoresis through 1% agarose, 2.2 M formaldehyde gels, transferred to nylon membranes (Hybond-N, Amersham, Arlington Heights, Ill.) and fixed by baking at 80° C. for 2 hrs. The probes used for hybridization were:

(1) PstI 3' fragment of FTH cDNA (530 bp);
(2) T16 specific SPF-16R PCR cDNA product.

After hybridizations with $^{32}$P-labeled probes (10$^6$ cpm ml) 42° C., 50% formamide 5×SSC, blots were washed in 2×SSC, 0.1% SDS at 25° C., followed by 0.1×SSC, 0.1% SDS at 55° C.

Human tissues mRNA was purchased from Clontech (Cat. # 7760-1) and hybridized according to the manufacturer's instructions.

EXAMPLE 4

Detection of OFF1 Transcripts by RT-PCR in Peripheral Blood

I. Preparation of Blood Derivatives

Tube A. To whole blood (0.5 ml) 1 ml red blood cell lysis buffer (Boehringer) was added at room temperature and mixed by inversion (without vortex). The preparation was then stored for 10 mins. at room temperature with agitation, and centrifuged at 2,500 rpm for 5 mins. at room temperature. The pellet was then washed with PBS.

Tube B 4.5 ml whole blood were centrifuged for 5 mins. at room temperature, at 1,030 g. In order to buffy coat, about 0.5 ml lysis buffer 1 ml was added for 10 mins. at room temperature. The mixture was placed on a shaker, and then centrifuged at 2,500 rpm for 5 mins. at room temperature. The pellet was finally washed with PBS.

Tube C To 5 ml of whole blood 10 ml of PBS were added. Mononuclear bells were isolated by density centrifugation on Ficoll hypaque (5 ml), and spun at 450 g for 25 mins. at room temperature. The pellet was washed with PBS (resulting in about 5×10$^6$ lymphocytes).

II. Isolation of RNA (According to Tri-reagent Protocols Supplied by the Manufacturer)

1. Cells were lysed with Tri Reagent; To Tube A—0.5 ml were added, to Tubes B and C 1 ml was added by repetitive pipetting.

2. The preparation was stored for 5 mins. at room temperature, and then 0.2 ml chloroform per 1 ml of Tri Reagent were added and vortexed for 5 secs. The resulting preparation was stored for 2–15 mins. at room temperature and centrifuged 12,000 g 15 mins. at 4° C.

3. The aqueous phase was transferred to a fresh tube, and precipitated by 0.5 ml isopropanol per 1 ml TRI Reagent on ice for 5–10 mins. (or at room temperature) and centrifuged 12,000 g at 4° C.

4. The supernatant was removed and the RNA pellet was washed with 75% ethanol by vortexing and centrifugation.

The RNA pellet was air dried and then dissolved in 20 μl DEPC-water, RNA has O.D. at 260/280=1.6-1-9 yield=2.5 μg (for Tubes B and C).

III. RT-PCR

1 μg RNA (or 14 μl whole blood RNA of Tube A) was placed in total volume of up to 15 μl in DEPC water, heated at 70° C. for 10 mins. and cooled immediately on ice. Then it was spun briefly and 10 μl of mix was added a follows: 5 μl M-MLV RT 5× Reaction buffer; 1 μl dNTPs (12.5 μl); 1 μl Recombinant Rnasin Ribonuclease (20 u); 2 μl DEPC water; 1 μl M-NLV Reverse transcriptase (RT) (200 units).

The mixture was incubated for 60 mins. at 37° C. followed by 10 mins. at 70° C. to stop the reaction.

PCR

For PCR the following reagents were used: 1 μl cDNA (or 0.5 μl cDNA for PCR of normal ferritin (FTH) H (Chain); 5 μl 10× reaction buffer for DNA polimerase; 1 μl forward primer (~10 pmole); 1 μl reverse primer (~10 pmole); 1 μl dNTPs (12.5 mM), 0.5 u Taq polymerase from Appligen (0.1 μl); Takara 0.2 gel DDW water up to 50 μl.

The PCR program (cycles) was as follows:

| 1) 94°-2'          | 2) 50°-2' | 3) 72°-1' |
|--------------------|-----------|-----------|
| 4) 94°-1'          | 5) 50°-2' | 6) 72°-3' |
| 7) 29 times to 4   | 8) 94°-1' | 9) 50°-2' |
| 10) 72°-10'        | 11) 4°.   |           |

PCR products were identified by electrophoresis on 1% agarose gel and 0.10 μg ethidiumbromide.

Since T16 transcripts do not yield bands after the first PCR, in order to amplify the results the initial PCR is followed by nesting PCR, using 1 μl of PCR 1 diluted 1:100 in the above PCR program.

As an example, the following primers were used for nesting PCR.

PCR1: XIF → 16R nesting PCR2: 17F → SPR

For normal ferritin 17F → 3'R yields a visible product.

No nesting is required.

RESULTS

EXAMPLE 5

Isolation of cDNA Clones

Five cDNA clones were isolated from T47D breast cancer cells cDNA library (T) and 15 cDNA clones were isolated from placenta cDNA library (P). The two clones with the largest inserts (1 KB) were T16 from T47D breast cancer and p4, 7 from placenta.

The sequence of the full length cDNA (0.9 KB) from clone T16 revealed a sequence of 890 bp; 109 bp in the 5' UTR 495 bp (165 aa) in the coding region and 286 bp in the 3' UTR. Full sequences are shown in FIG. 1.

The nucleic acid sequence of cDNA from clone p4, 7 revealed a sequence of 890 bp which is completely homologous to the known FTH sequence (as compared in FIG. 2) and represents a normal ferritin heavy chain (Cohen et al., 1996, Drysdale 1988). Partial homology was found between clone p4, 7 and clone T16 (FIG. 2A, 2B). The homologous sequences were clone 4, 7 139–511 and clone T16 87–460. The later included 22 bp in the 5' UTR followed by 351 bp (117 aa) in the above coding region. No further homology was found between the above two clones. As can be seen in FIGS. 2A and 2B, homology is indicated by a broken line.

EXAMPLE 6

Comparison to Gene Bank Data

Comparison of the new sequence of T16 to sequences in the Gene Bank and EMBL database shown only a segment from 463–671 bp matching a segment of human mitochondria cytochrome oxidase I (COI) 6486–6694 bp (FIG. 3). However, the predicted 48 amino acids of T16 did not match the CO I sequence. There was no further homology found in the Gene Bank for T16; 671–890 bp or I-87 bp.

EXAMPLE 7

PCR Amplification of a T16 Compatible Placental cDNA

A placenta λgt11 cDNA library was used to amplify by PCR a T16 compatible cDNA from placenta. This was performed using the T16 specific primers i.e. λgt11 F (1060) or λgt11 R (1061) and primer 16R for the 5' end and primer SPF for the 3' end (Table 1; FIG. 7) schematically as shown below:

```
1060  5'——16  3'        5'  SPF——1061  3'
```

The PCR products obtained from the placenta cDNA library using the above T16 (presented in FIG. 4). There was only a small difference in the 5' non coding region which included 2 single nucleotide substitutions, as well as a single base insertion and one deletion (FIG. 4).

Verification of the sequence was carried out on cDNA obtained from RNA by reverse transcriptase and PCR amplification (RT-PCR). The RNA was isolated from human T47D breast cancer and HBL 100 breast epithelial cell lines, and from human peripheral blood lyphocytes ((PBL), non activated and from concanavalin activated PBL.

RNA (5 μg) from the different cells was used to prepare cDNA by reverse transcriptase using random primers. T16 cDNA as amplified by PCR using the following primers: 5' BNCF and 3' 16R (Table 1; FIG. 7), followed by nesting with the primers 5' BNCF-3' 17R and 5' 17F-3' 16R (Table 1; FIG. 7).

```
5'  BNCF——16R  3'  1st PCR
5'  BNCF----17R  3'  nested PCR
5'  17F----16R  3'  nested PCR
```

Nesting was necessary since the first PCR amplification did not yield a visible PCR product.

The sequences obtained from the isolated cDNA products from the above cell sources revealed that all of them including T47D breast cancer had a sequence identical with the sequence obtained from the T16 homologous cDNA from placenta (FIG. 4), i.e. it included the substitution insertion and deletion in the non-coding region.

These results suggest that the sequence differences in the T16 cDNA clone isolated from the T47D cDNA library were a mistake occurring in the formation of the library. The final nucleotide sequence of T16 and the deduced amino-acid sequence are presented in FIG. 5.

EXAMPLE 8

Expression of T16 in Various Tissues

Figure 6A:
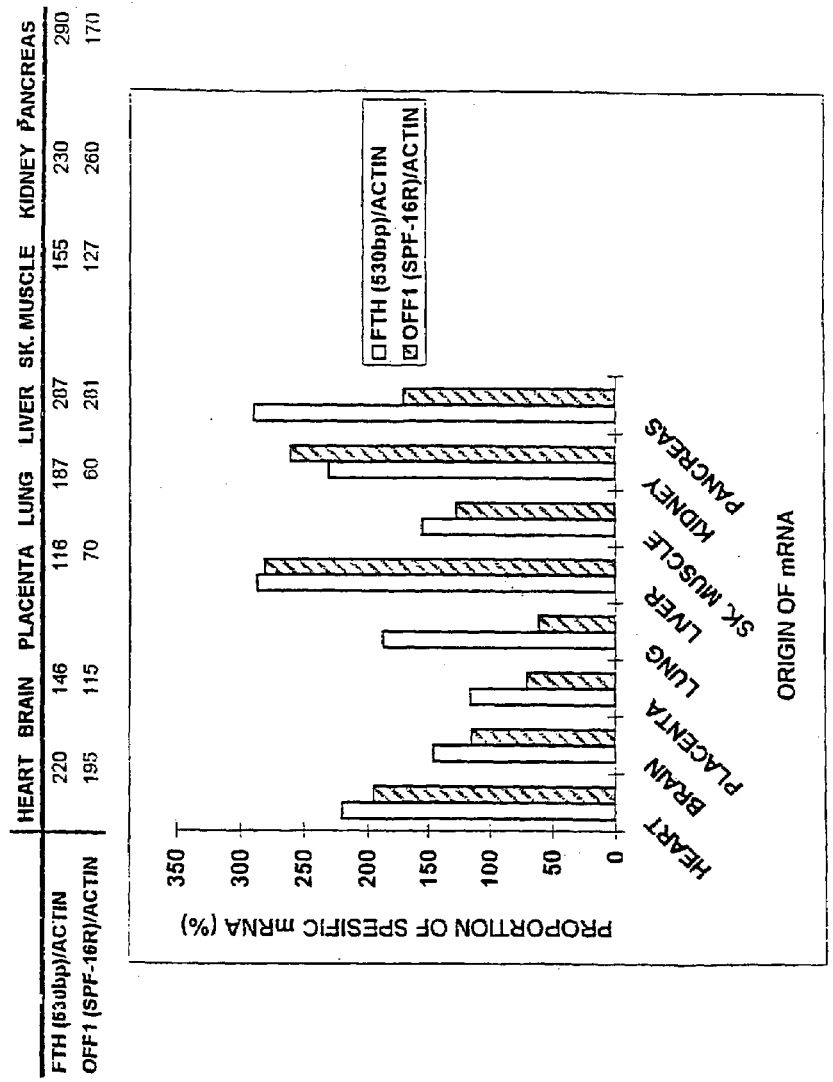
FIG. 6A shows the relative expression of FTH in mRNA and OFF1 RNA among total mRNA isolated from different tissues and optimized with β-actin expression.
Figure 6B:
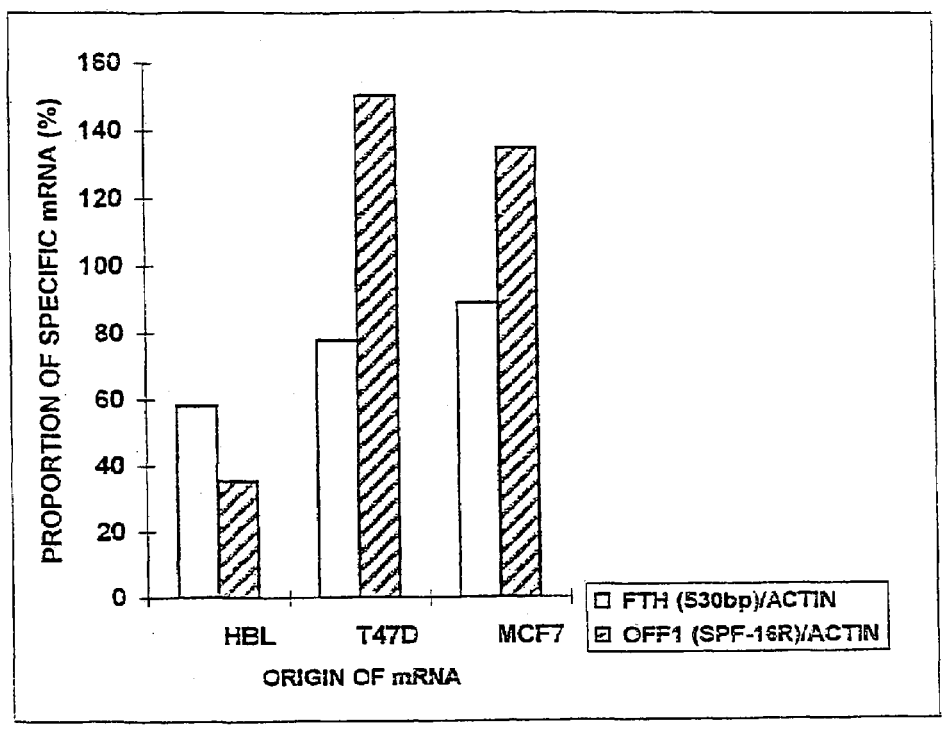
FIG. 6B shows the relative expression of FTH mRNA hybridized with $32^P$PstI 3' fragment of liver FTH cDNA (530 bp), from either normal HBL human lactating breast or from cancer cell lines (MCF-7 and T47D)

The expression of T16 gene in a variety of human tissues, including breast epithelial and breast cancer cell lines were analyzed by northern blotting, according to state of the art procedure and the results are shown in FIGS. 6A and 6B.

The northern blot revealed a 0.9 kb transcript in all the cells tested.

However, as seen in FIGS. 6A, 6B, the relative expression of T16 mRNA and FTH revealed that there was over-expression of T16 mRNA only in breast cancer cells indicating that the T16 can be used as a marker for breast cancer.

The relative amount of each tissue mRNA indicates that all the peaks on the blot for a single probe FTH (normal H chain) or T16 (OFF1) amount to 100% and therefore each mRNA bar represents a ratio relative to the other tissues. In order to ensure that the amount of RNA loaded into the gel is equal, a household gene i.e. actin was probed. The numbers are corrected according to ratio of actin. On the same blot therefore if both mRNA (FTH and T16 (OFF1)) are expressed similarly (if one is low/or high the other is also low/or high) then there is no difference in expression between the two mRNAs. However, only in breast cancer there is evidence that T16 (OFF1) is high as compared with FTH but not in HBL cells which is a cell line derived from normal lactating breast. These results clearly indicate that the method of detecting OFF1 is valid for differentiating between breast cancer and cells derived from normal lactating breast.

EXAMPLE 9

Preparation of OFF1—Fusion Protein

Materials and Methods

Construction of *E. coli* Strains Expressing Glutathione S-Transferase (GST) and OFF1 Fusion Proteins The expression vector (pGEX-5X-1) used for gene fusion construction was the GST Gene Fusion System (Pharmacia). The OFF1 coding region (designated as "FL", full-length) of about 0.5 kb was prepared by PCR with the following 5' end primer:

```
5' GT GGGATCCC CCATGACGACCGCGTCCA    (1-27 of
      BamHI                            SEQ ID NO:33),
``` in order to add a BamHI site 1 base upstream from the start codon ATG and with the 3' end primer

```
5' CCCG CTCGAG TCA GGG TGA CCG AAA AAT CAG 3'  (SEQ ID NO:36)
       XhoI
``` in order to add an XhoI site after the stop codon TAA using the PCR kit (Perkin-Elmer/Centus).

A deletion construct for encoding the unique C-terminal 48 aa, designated as "C48", of the OFF1 was also prepared from "FL" OFF1 PCR product, by cleavage with restriction enzymes 5' ECORI and 3' XhoI. The PCR program was as follows (cycles):

1. 94°—2 min.
2. 94°—1 min.
3. 50°—2 min.
4. 72°—3 min.
5. followed by 28 times
6. 94°—1 min.
7. 50°—2 min.
8. 72°—10 min.

The PCR products were gel-purified and then ligated into the pGEX 5X-1 plasmid at 5' BamHI and 3' XhoI sites. The resultant recombinant plasmids can produce fusi8on proteins in which the N-terminus is the GST and the C-terminus is the OFF1, or c48 of OFF1. E. coli strain BL-21 was transformed with the vector alone or the two recombinant plasmid DNA to produce pGST cells, pGST-FL cells, pGST-C48 cells following the standard protocol (Maniatis Sambrook J. Fritch E F & Maniatis T., Molecular Cloning: A Laboratory Manual (1989) (Cold Spring Harbor Lab. Press Plainview, N.Y. Snd Ed.)).

Growth of E. coli Cells and Expression of OFF1 Fusion Protein in E. coli

Wild-type and transformed E. coli cells were grown in Luria-Bertani (LB) broth containing 100 µg/ml of ampicillin at 37° C. overnight. The overnight cultures were diluted 1000-fold using fresh LB broth plus ampicillin, and incubation continued at 37° C. For growth curve determination, samples were taken every 30 mins. to measure the optical density at 600 nm. To test the induction conditions for fusion protein expression, the diluted overnight cultures were grown at 37° C. until mid-long phase (3–4 h, or $OD_{600}=\approx 0.6$). Isopropyl β-D-thiogalactopyranoside (IPTG) was then added to a final concentration of 1 mM, and incubation was continued at 37° C. for 4 hours. After IPTG induction, the cultures were harvested and cell pellets were obtained by centrifugation. Pellets were resuspended in 100 µl of Laemmli sample buffer. Thirty micrograms of protein samples, determined by the Bradford assay, was subjected to SDS/PAGE.

SDS/PAGE and Western Blot Analysis

One-dimensioned SDS/PAGE was performed according to Laemmli using 12.5% (wt/vol) polyacrylamide gels. For immunoblotting, proteins were transferred from polyacrylamide gels to immobilon polyvinylidene difluoride membranes (Millipore) with Tris/glycine electroblotting buffer according to Towbin et al.[29]. Protein bands cross-reacting with CM-H-9 monoclonal antibody (MoAb) were identified by reaction with horseradish peroxidase conjugated with goat anti-mouse IgG (Bio-Rad). The conditions of immunoreactions were according to the manufacturer's specification (DAKO).

Method for Preparation of OFF1 Recombinant Protein

Day 1:

Inoculate a single colony of transformed bacteria into 50 ml LB-Borth (with the appropriate antibiotics) and grow overnight.

Day 2:

Add the 50 ml culture to 1000 ml LB-Borth (with the appropriate antibiotics) and grow for 2 hrs at 37° C. (around 0.8 O.D.).
Add this culture 100 µl of IPTG (stock solution of 1M) and continue growth for 4 hrs at 37° C. for 5 hrs at 30° C.
Centrifuge for 20 mins. at 4° C., 4000 rpm with rotor GS-3.
Discard the supernatant and suspend in 20 ml ice cold PBS+0.1% Triton-X100.
Sonicate 90/7 for 10 sec, three times on ice (in 50 ml tube)
Spin 2300 rpm at 4° C. for 10 min.
Collect supernatant in 50 ml Falcon tube
Add 1 ml of Glutathion-Sepharose 4B Beads (stock 50% beads in PBS).
Incubate for 5–30 min. at RT or overnight at 4° C. with rolling.
Collect the beads by centrifuging 1 min, 2000 rpm.
Wash the beads 3 times with ice cold PBS.
Elute protein with 1 ml of 50 mM Tris-HCl pH 8 containing 15 mM Glutathione and 10 mM DTT.
Dialyze (twice) against PBS containing 30% Glycerol.
Store aliquots in –20° C.

Figure 9A:
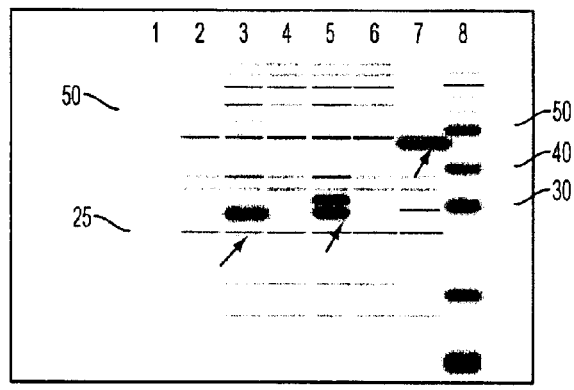
FIG. 9A shows SDS-PAGE (12%) of total cell lysates (lane 2) 10 μl from E. coli containing the vector pGEX alone or the pGEX constructed to contain C48 fragment (lane 4) or total constructs containing full length OFF1 (lane 6). The recombinant proteins are marked by arrows.
Figure 9B:
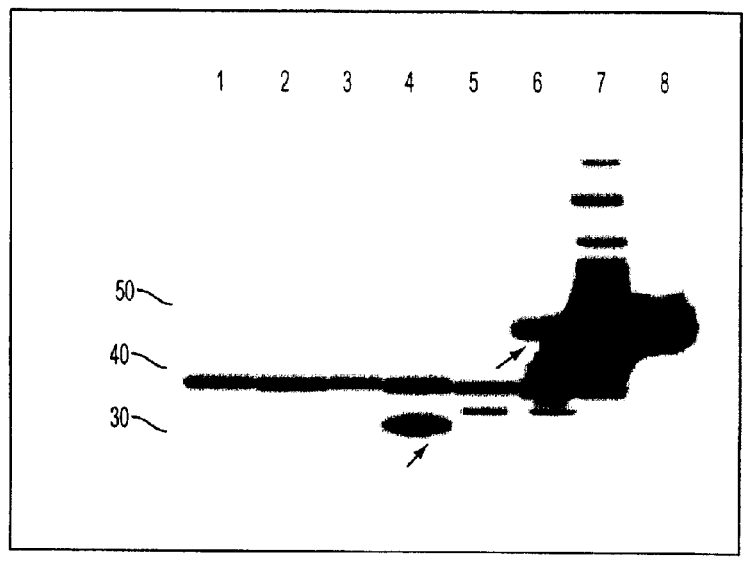
FIG. 9B shows the same as FIG. 9A but reactive with CMH-9 in antibodies (lanes 4 and 6 indicating presence of protein)

The results are shown in FIGS. 9A and 9B and clearly indicate (also with verification of binding to specific monoclonal antibodies) that recombinant protein was expressed in the host cell.

EXAMPLE 10

Expression of T16 Gene as a Biomarker in Breast Cancer

The presence and over expression of T16 transcript in breast carcinoma is consistent with the differential cDNA cloning strategy which suggest its utility as a biomarker in breast cancer detection.

25 patients suspected of having cancer were tested for their T16 transcript by using RT-PCR in their peripheral blood as described in the experiment.

All 25 patients underwent biopsy and their condition assessed independently by the pathology department of Rabin Medical Center, Israel. The results are shown in Table 2, wherein (−)=no product, (±)=very faint band, (+) or (++)=strong bands.

As can be seen, of the 13 cancer patients 12 were identified by over expression of T16 with a single false-negative result (Case 12) which was clinically assessed as having cancer and not diagnosed by T16 over expression. These results indicate a false-negative level of about 9%. Of the 15 patients positively identified by the T16 transcript, 3 were not clinically diagnosed as having cancer, i.e. three false-positive results, indicating a 20% level of false-positive results.

TABLE 2

PCR Amplification of T16 transcripts in blood of patients with suspected breast cancer

| No. | RTPCR 17-SPR* | Diagnosis of breast biopsy | Remarks |
|---|---|---|---|
| 1 | ++ | Inf. Duct Ca T 1.6 No/12 | Cancer |
| 2 | − | Fibrocystic Disease | |
| 3 | − | Fibrocystic Disease | |
| 4 | + | Inf. Duct Ca | Cancer |
| 5 | − | Fibrocystic Disease | |
| 6 | − | Fibrocystic Disease | |
| 7 | ++ | Inf. Duct Ca GII T1.4 No/11 | Cancer |
| 8 | ++ | Lobular Ca In-Situ | |
| 9 | − | Fibrocystic Disease | |
| 10 | − | Atypical hyperplasia | |
| 11 | + | Inf. Duct Ca GIII T1, 2 N? | Cancer |
| 12 | − | Inf Duct Ca GII T2 No/8 | Cancer |
| 13 | + | Atypical hyperplasia + Fibrocystic Disease | |
| 14 | + | Inf. bular Ca. T1.8 N1/10 | Cancer |
| 15 | +− | Large lactiferous ducts. Periductal lymphoid Inf. | |

TABLE 2-continued

PCR Amplification of T16 transcripts in blood of patients with suspected breast cancer

| No. | RTPCR 17-SPR* | Diagnosis of breast biopsy | Remarks |
|---|---|---|---|
| 16 | ++ | Inf. Duct Ca T2 No/15 | Cancer |
| 17 | + | Inf. Duct Ca T2 No/8 | Cancer |
| 18 | + | Fibrocystic Disease | |
| 19 | ++ | Inf. Duct Ca GII T2.5 N/9 | Cancer |
| 20 | + | Inf. Duct Ca GIII T1 No/8 | Cancer |
| 21 | − | Fibrocystic Disease Ductectasia | |
| 22 | + | Introductal papillary Ca T0.5 | |
| 23 | ++ | Inf. Duct Ca GII T1 No/15 | Cancer |
| 24 | − | Fibrocystic prol. Ductectasia Atypical hyperplasia | |
| 24 | + | Inf. Duct Ca GII–III T2 No/13 | Cancer |

*Amplification of T16 mRNA transcripts in blood of patients prior to breast biopsy
(−) No PCR product (+−) Very faint PCR product (+), (++) Positive PCR product

EXAMPLE 11

The Effect of OFF1 on Granulocyte-monocyte Propogation Cells

OFF1 was purified from term placenta as previously described in U.S. Pat. No. 4,882,270 and U.S. Pat. No. 4,954,434 and will be termed hereinafter also as p43.

Mouse, MoAb, CM-H-9 was produced against human placental ferritin as previously described in the above two U.S. patents. The MoAb was obtained from ascites fluid following precipitation with 50% saturated ammonium sulphate solution, and purification on sephadex G-200 colomn.

CFU-GM Assays

Bone marrow samples from 11 healthy volunteer donors were processed by density gradient separation using Histopaque-107 (Sigma diagnostics, St. Louis, Mo., USA) to obtain a purified population of mononuclear cells. Colony assays were performed in a plating medium containing final concentrations of 0.92% methyl cellulose (M-281 powder, 4,000 centipoise, Fisher Scientific Co., Fair Lawn, N.J., USA), rehydrated in Iscove's modified Dulbecco's medium containing 36 mM sodium bicarbonate (Gibco, Grand Island, N.Y., USA), 30% fetal bovine serum (FBS) (Hy-Clone, Logan, Utah, USA) 0.292 mg/ml glutamine, 100 U/ml penicillin and 0.01 mg/ml streptomycin (Biological Industries, Beit Haemek, Israel).

Growth factors used were 15–30 mg/ml GM-CSF Leucomax (Sandoz Pharma) and 5% vol/vol human phytohemagglutinin-M (Difco Laboratories, Detroit, Mich., USA)-induced conditioned medium (Cond. Med.) p43 (PLF) was added at concentration of 1 μg/mL and in neutralization experiments, p43 (PLF) was preincubated with 10× excess of CM-H9 MoAb at 37° C. for 30 min and the complex added to the assay as above.

The colony assay medium contained $10^5$ mononuclear cells/ml and each 1 ml was plated into triplicate wells (333 μl/well) of a 24 well tissue culture plate (Greiner, Germany). Water was added to spaces between cells to maximize humidity during incubation of the cultures. The cultures were incubated at 37° C. in 5% $CO_2$ and 55% relative humidity. Plates were scored after 14 days for colonies containing more than 50 cells.

RESULTS

Figure 10:
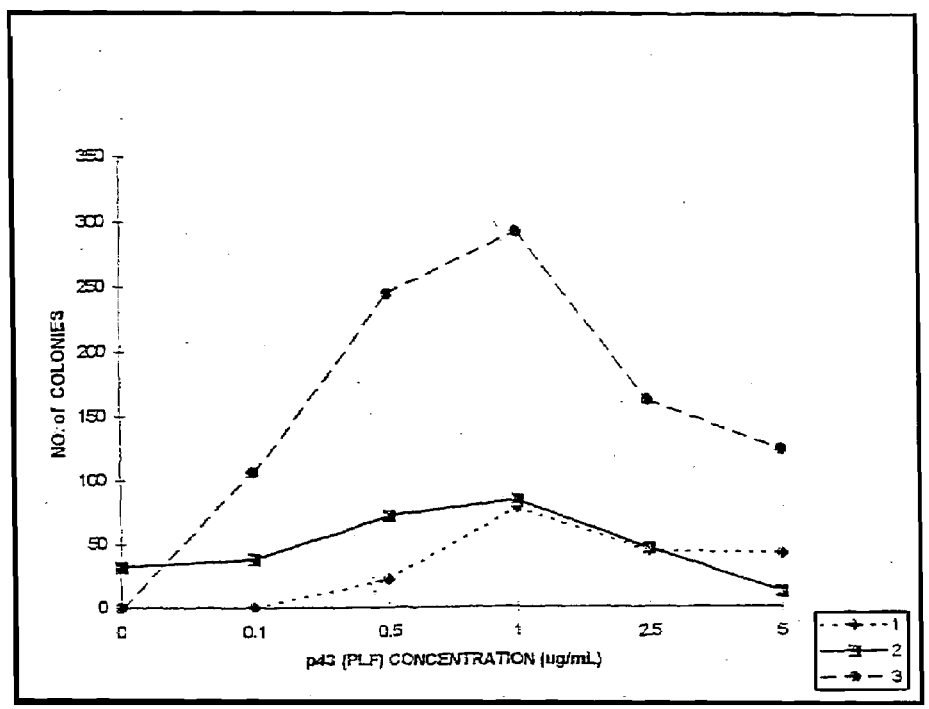
FIG. 10 shows the effect of the protein of the invention on CFU-GM colony formation obtained from three healthy donors.

Effect of OFF1 Protein (p43 (PLF)) on Human CFU-GM Growth in-vitro: Dose Response (p43 (PLF)) was tested for its capacity to influence colony formation of human bone marrow progenitor CFU-GM. p43 alone exhibited a concentration dependent stimulatory effect on bone marrow progenitor cells obtained from three donors. The highest number of colonies was obtained with 1 μg/1 mL of p43 (FIG. 10). At higher concentrations the number of cells was lower. All subsequent experiments were further carried out at concentration of 1 μg/mL of p43 (PLF).

Comparison of the Stimulatory Effect of p43 (PLF) and GM-CSF

Figure 11:
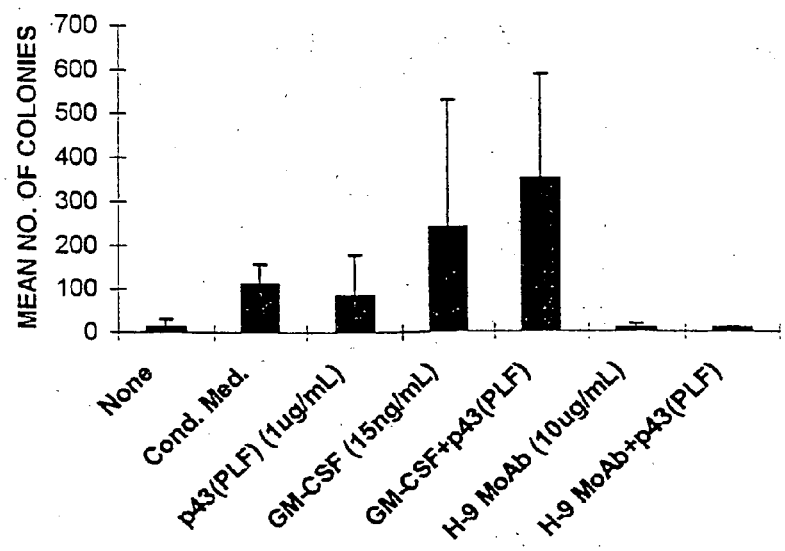
FIG. 11 shows the effect of the protein of the invention and its combination with GM-CSF or CMH9 Moab on CFU-GM colony formation.

The mean number of colonies obtained following treatment of bone marrow cells from 11 donors with p43 (PLF) was 169+/−216 significantly higher (p=0.028) than in medium only (18+/−21) (Table 3). The stimulatory effect of p43 (PLF) was abolished following preincubation with its specific MoAb CM-H9 Mean CFU-GM—7+/−10) (FIG. 11). The number of colonies obtained with p43 (PLF) was not significantly different than the number obtained with Cond. Med. (227+/−223) or with GM-CSF (276+/−257) (Table 3). When the treatment combined both GM-CSF (15 ugr/mL) and p43 (PLF) the mean number of colonies obtained with the mixture increased to 353+/−236 colonies, but it did not reach a statistical significance compared to each factor alone.

It is concluded that p43 (PLF) known to act as an immunosuppressive cytokine is active as a growth factor on human bone marrow progenitor cells.

TABLE 3

The effect of p43 (PLF) on the generation of CFU-GM formation by normal human bone marrow. Comparison with conditioned medium and with GMCSF.

| | TREATMENT | | | |
|---|---|---|---|---|
| Bone Marrow No. | None | Cond. Med. | p43 (PLF) (1 μg/ml) | GM-CSF (15 ng/ml) |
| 1 | 8 | 522 | 280 | 144 |
| 2 | 46 | 758 | 748 | 396 |
| 3 | 46 | 322 | 152 | 114 |
| 4 | 2 | 90 | 28 | 66 |
| 5 | 2 | 134 | 94 | 136 |
| 6 | 8 | 170 | 6 | 250 |
| 7 | 0 | 52 | 0 | 50 |
| 8 | 4 | 102 | 242 | 74 |
| 9 | 0 | 54 | 8 | 520 |
| 10 | 34 | 170 | 210 | 884 |
| 11 | 48 | 126 | 94 | 405 |
| AVG. | 18 | 227 | 169 | 276.2 |
| STD. | 21 | 223 | 216 | 257 |
| MEDIAN | 8 | 134 | 94 | 144 |
| RANGE | 0–48 | 52–758 | 0–748 | 50–884 |

EXAMPLE 12

Effect of C48/OFF1 on Induction of TH1/TH2 Cytokine Secretion

Studies of animal models of organ-specific autoimmune diseases suggest that a cascade of autoreactive T helper 1 (Th1)-type inflammatory responses mediates the disease process. Although the initial autoimmune response is limited in its recognition of self-antigens, it subsequently expands to react with additional target tissue antigens.

Based on the antagonistic functions of different T-cell subsets, a paradigm became popular which held that induced regulatory responses (such as Th2 cells) could be used to downregulate proinflammatory pathogenic autoimmune responses and inhibit disease progression. A polypeptide encoded by the DNA molecule of the invention may be used for this purpose.

Methods

In-vitro activation of human lymphocytes without and with C48/OFF1 treatment was carried out in a mixed lymphocyte culture (MLC). Human peripheral blood lymphocytes ($2\times16^6$/ml) (responder cells) were incubated with non-related Mitomycin C (40 µgr/ml) treated lymphocytes ($2\times10^6$/ml) in RPMI-1640 medium containing 10% Fetal Calf serum and antibiotics. The cultures were incubated for 24 h in a humidified incubator at 37° C. with 5% $CO_2$. Supernatants were collected and the concentration of the secreted cytokines were measured using an ELISA assay kit. The level of IL-2 R, and interferon (Th1 cytokines) and IL-6 and IL-10 (TH2 cytokines) were determined.

Figure 12:
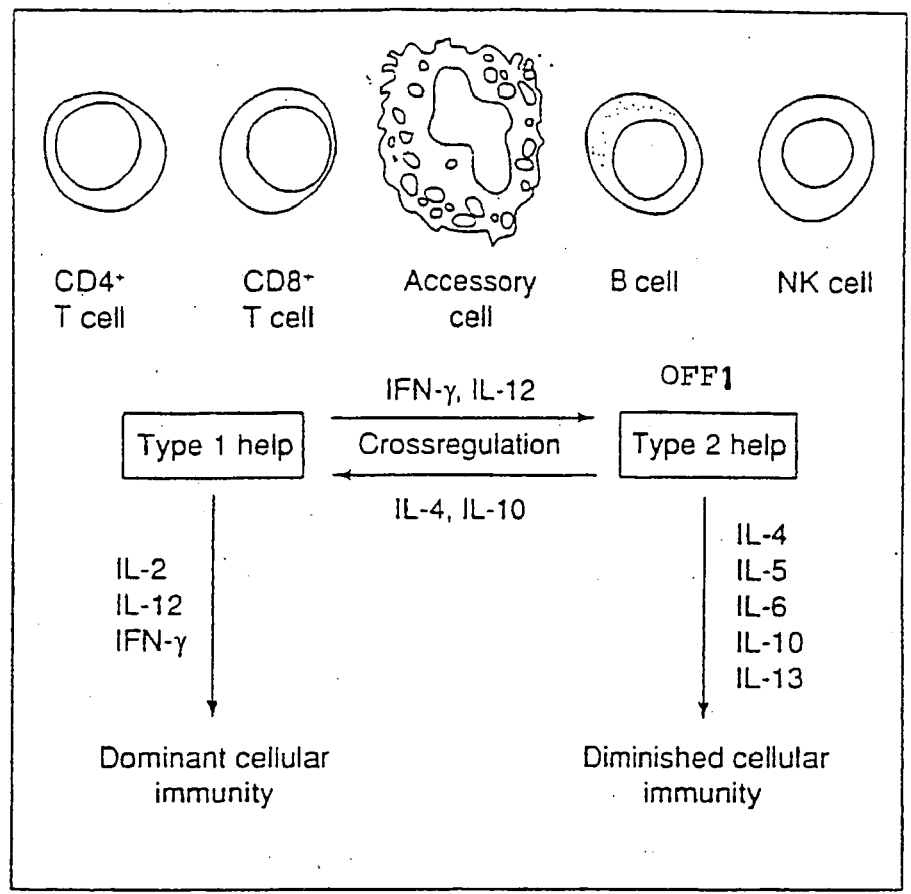
FIG. 12 shows a scheme summarizing the effect of OFF1 on immunoregulation.

As may be seen in Table 1, activation of lymphocytes following treatment with C48 (OFF1) induced the secretion of exceedingly high levels of IL-6 and IL-10 (TH2-type), which are known to inhibit type 1 immune responses (IL-2 and Interferon γ) as indicated in FIG. 12.

TABLE 4

Effect of C48/OFF1 on cytokine secretion by activated human lymphocytes in MLR in-vitro.

| | (1) Treatment of MLR | |
| --- | --- | --- |
| Cytokine (u/mL) | None | C48/OFF 1 |
| sIL-2R | 50 | 50 |
| γ Interferon | 53 | 46 |
| IL-6 | 20,580 +/− 1892 | 170,779 +/− 58,800 |
| IL-10 | 54 +/− 23 | 1125 +/− 332 | sIL-2R = Soluble interleukin 2 receptor

It is therefore concluded that C48/OFF1 induces preferentially a TH2 type immunoresponse associated with diminished cellular immunity.

EXAMPLE 13

Effect of C48 (OFF1) on Zymosan Induced Arthritis (ZIA) in Mice

Materials and Methods

Animals: Female ICR mice were obtained from our institution's breeding facilities and were fed a standard diet and tap water ad libidum.

Induction of zymosan-induced arthritis: A homogeneous suspension of 25 mg zymosan A (*Saccharomyces cerevisiae*), dissolves in 1 ml endotoxin-free saline, was obtained by boiling twice followed by sonic emulsification. Arthritis was induced by intrarticular injection of 0.5 mgr/20 l zymosan into each right and left knees.

Assessment of ZIA: Mice were evaluated at 14 days post zymosan injections: Swelling was quantitated by measuring the thickness of the knees with a caliper, at $14^{th}$ day post ZIA and compared to the thickness prior to ZIA.

Histologic processing and analysis of knee joints: Knee joints were dissected, fixed, decalcified, dehydrated, and embedded in paraffin. Standard frontal section of 7 µm were prepared and stained with eosin-hematoxilin.

Disease severity was assessed by calculation of arthritic index as follows:

Semiquantitative assessment of pathologic findings was performed using a grading system, consisting of five grades. Grade 0: normal synovia; grade 1: 1–5 cellular infiltrates in the microscopic field; grade 2: 6–20 cellular infiltrates; grade 3: 21–50 infiltrates; grade 4: more than 56 cells.

Lymphocytic nodules: grade 1: 1–3 nodules per sectio; grade 2: 4–10 nodules; grade 3: 11–20 nodules; grade 4: more than 20 nodules.

Histiocytes grading: grade 1: 1–10 cell; grade 2: 11–20 cells; grade 3: 21–30 cells; grade 4: more than 30 cells.

Synovial thickness: grade 0: presence of 1 layer of synovial cells; grade 2: 2–3 layers; grade 3: 4–6 layers; grade 4: more than 6 layers.

The presence of pannus was considered evidence of severe synovitis.

Treatment with C48 (OFF1): Three groups of 10 mice each, were treated by daily intraperitoneal injections of either PBS (control group) or C48 (30 µg/per mouse).

Statistical analysis: The significance of comparisons between means was assessed by Student's t-test.

RESULTS

Effect of C48 administration on ZIA: Two group of mice (n=10 each) were treated by daily i.p. injections from day 1 up to 10 (10 days), or from day 3 to 10 (7 days) (C48 delayed) following intraarticular zymosan injections. Groups of ZIA mice (n=10) which received daily injections of PBS served as control.

Arthritis developed in 100% of control vehicle PBS treated mice within 14 days post zymosan injections. Mean knee joint swelling of the control group was 1.24 mm whereas C48 (OFF1) treatment reduced the mean swelling to 0.24 mm or to 0.33 mm in the C48 delayed treatment. (Table 5).

TABLE 5

Effect of C48 treatment on knee swelling of ZIA in mice

| Mouse Treatment | Knee swelling (mm) Mean +/− SD (n = 10) | Significance $p^1$ |
| --- | --- | --- |
| PBS (control) | 1.24 +/− 0.59 | |
| C48 | 0.24 +/− 0.56 | 0.001 |
| C48 delayed | 0.33 +/− 0.57 | 0.002 |

[1]p = Significance of difference from control by student's t test.

Administration of C48 from day 1 to 10 or from day 3 to 10 significantly reduced the severity of arthritis to very mild compared with ZOA mice treated with PBS alone, as indicated by the arthritic score (Table 6).

TABLE 6

Effect of C48 treatment on disease severity of ZIA in mice

| Mouse Treatment | Arthritis Score[1] Mean +/− SD (n = 10) | Significance $p^2$ |
| --- | --- | --- |
| PBS (control) | 1.7 +/− 0.78 | |
| C48 | 1 +/− 0.83 | 0.0008 |
| C48 delayed | 0.9 +/− 0.83 | 0.0001 |

[1]Score represents the mean grades of pathological findings.
[2]p = Significance of difference from control by Student's t test No significant difference was found between the groups of mice treated with C48 (OFF-1) between day 1 to 10 or only from day 3 to 10.

EXAMPLE 14

Protocol for Treatment with c48/OFF1 of Patients with Rheumatoid Arthritis

Patients: Men and women 18 years of age or older with rheumatoid arthritis according to the criteria of the American College of Rheumatology.

Treatment: Patients may be treated with c48 or OFF1 at a dose of e.g. 0.5–5 mgr per kilogram weight injected subcutaneously twice weekly for three months. Other treatment protocols may be determined by those skilled in the art. Treatment may be repeated with disease recurrence.

EXAMPLE 15

Therapeutic Agent in Transplantation

Successful transplantation of organs requires the use of agents capable of suppressing the immune response against alloantigens.

Use of these nonspecific immunosuppressive drugs, however, can lead to the development of opportunistic, infections or secondary cancer. For this reason, a way of specially suppressing alloreactive T cells without inhibiting the entire T cell repertoire is an important goal of transplantation immunology.

In the case of bone marrow transplantation (BMT), T cells in the donor marrow are the cause of graft-versus-host disease (GVHD). We hypothesized that the induction of anergy in donor T cells that have the potential to react against the recipient's alloantigens might ameliorate GVHD while preserving the rest of the T cell repertoire.

The present treatment protocol was undertaken to develop ex-vivo treatment with OFF1 to induce a state of alloantigen-specific tolerization resulting in the lack of GVHD generation in vivo and development of bone marrow chimerism.

Methods

Animals: C57BL/6 ($H2^b$) and BALB/c ($H2^d$) mice were purchased from Harlane. Donors and recipients were 8–10 wk of age at the time of BMT. All mice were housed in a specific pathogen-free facility in microisolator cages.

Ex-vivo induction of anergy in mixed lymphocyte reaction (MLR): C57Bl donor bone marrow (responder) was harvested 2 days before transplantation. Balb/c recipient (stimulator) spleen cells were irradiated at a midplane dose of 3300 cGy. The cells were resuspended in RPMI-1640 medium with 5% mouse serum to $4\times10^6$/ml and incubated with 1 µg/ml of OFF1 for 30 min.

The erythrocyte depleted mononuclear cell fraction of the marrow was resuspended at a concentration of $4\times10^6$/ml in the above medium in a Donor:Recipient ratio of 1:1. The cells were cultured in tissue culture flasks for 36 hours at 37° C. in 5% CO2, washed and resuspended to $2\times10^7$ cells/1 ml in PBS containing OFF1 (1 µg/ml).

Bone marrow Transplantation (BMT): Balb/c recipients were sublethely irradiated by exposing mice to 5;5 GRAY total body irradiation from a $^{137}$Cesium source at a dose rate of 85 cGY/min.

Day 2 MLR cultured cells ($10^7$/0.5 ml) were injected intravenously to BALB/c mice pretreated with OFF1 ((10 µg) injected i.p.) (BMT+OFF1). Control mice were injected with MLR bone marrow cells treated with PBS.

Mice were treated for 14 days by i.p. injection of 10 µg OFF1. Control mice were injected with PBS (BMT+PBS)

Flow cytometry: Bone marrow (B.M.) and splenocytes (spl.) were removed from transplanted Balb/c mice 6 weeks post transplantation and tested with anti-$K^b$ monoclonal antibody for the presence of C57Bl Donor lymphocytes.

All results were obtained using FACS (Beckton Dickenson). Forward and side-scatter setting were gated to exclude debris. 10,000 cells were analyzed for each determination.

Immunologic assay: Splenocytes from bone marrow transplanted (BMT) Balb/c mice were reacted as above in MLR against the donor C57Bl splenocytes or against non-related splenocytes, to measure their immunoresponsiveness to the corresponding alloantigens.

RESULTS

In a representative experiment, (results not shown) a population of $K^b$ positive cells both in the bone marrow (BM) and in the spleen (Spl) was evident only in Balb/c ($K^d$) BMT treated with OFF1 and not in BMT treated with PBS (none). These results indicate that treatment of BMT with OFF1 resulted in development of hematopoietic chimerism.

EXAMPLE 16

Protocol for Transplantation of Anergic Haploidentical Bone Marrow in Human Patients Recipients: Patients with haploidentical bone marrow to the donor (i.e., marrow from a donor who shared only one or two major histocompatibility-complex haplotypes with the recipient).

Treatment: The patients undergo leukopheresis to collect 200 million to 600 million mononuclear cells per kilogram of body weight for use as the recipient's alloantigen-presenting cells. These cells are cryopreserved with the use of a standard method. Subsequently, the patient receive 1400 cGy of total-body irradiation followed by cyclophosphamide, and methylprednisolone.

Donor marrow is harvested two days before transplantation. Prophylaxis against GVHD consists of a short-course of cyclosporine starting on the day before transplantation, either by continuous infusion at 0.1 mg per kilogram per hour or by a bolus of 1.5 mg per kilogram over a period of 2 to 3 hours every 12 hours.

Ex Vivo Induction of Anergy

Cryopreserved mononuclear cells derived from recipient's blood are thawed, washed, and irradiated at a midplane dose of 3300 cGy. The cells are resuspended at a concentration of $5\times10^6$/ml in RPMI 1640 medium with 5% human AB serum. c48 or OFF1 is added at a concentration of 0.5–5 µg per milliliter for 30 minutes before the addition of the donor marrow cells. The erythrocyte-depleted mononuclear-cell fraction of the marrow is resuspended at a concentration of $5\times10^6$ cells per milliliter in RPMI 1640 medium with 5 percent human AB serum and added to the mixture of recipients cells and c48 or OFF1, in a donor:recipient ratio of 1:1. The coculture is incubated in tissue-culture flasks for 36 hours at 37° C. in 5 percent $CO_2$, washed, and then infused into recipient.

Engraftment of Anergic Haploidentical Bone Marrow

A median of 3 million CD34+ donor cells per kilogram of the recipient's weight are treated in the co-culture system, and a median of 2.2 million CD34+ cells per kilogram are infused into the recipient.

The transfused donor bone marrow may contain mature T cells, with medians of 28 million CD3+ cells per kilogram, including 14 million CD3+CD4+ cells per kilogram and 9 million CD3+CD8+ cells per kilogram, after the ex vivo treatment.

EXAMPLE 17

In-vitro Studies of Immunoresponse to Alloantigens

Splenocytes obtained from Balb/c mice ($K^b$) treated with BMT+PBS (control) and with BMT+OFF1 were used as responder cells (R) and were reacted with C57Bl ($K^b$) splenocytes as stimulator cells (S) in MLR.

As can be seen in Table 7, control mice (BMT+PBS) exhibited a high proliferation index (P.I.) in MLR at different S/R ratios. In contrast splenocytes obtained from the BMT+OFF1 chimeric mice were completely anergic and did not react at any S/R ratios.

However, splenocytes from chimeric BMT+OFF1 Balb/c mice responded in MLR against splenocytes from a non related alloantigen from ICR splenocytes, similarly to the response of control BMT+PBS (Table 7). The latter results indicate a specific anergy of BMT+OFF1 to the donor alloantigens but not to other non-related alloantigens.

TABLE 7

Immuneresponse of splenocytes from Balb/c mice transplanted with C57Bl bone marrow without and with OFF1 treatment.

| | | Bone marrow Recipient | |
| --- | --- | --- | --- |
| Stimulator | S/R Ratio[1] | BMT + PBS P.I.[2] | BMT + OFF1 P.I.[2] |
| (i)C57Bl | 0 | 1 | 1 |
| | 0.2 | 5.3 | 1.3 |
| | 1 | 3.6 | 1 |
| | 4 | 3.1 | 1.1 |
| (1)ICR | 0 | 1 | 1 |
| | 0.2 | 2.8 | 1.8 |
| | 1 | 3.6 | 2.6 |
| | 4 | 15.2 | 9.6 |

[1]S/R Ratio = Stimulator Responder ratio in MLR
[2]P.I. = Proliferation Index, compared with non activated cells (0)

In further experiments we tested the in-vitro effect of OFF1 treatment on responsiveness of splenocytes from control BMT+PBS against both donor C57Bl stimulators and against ICR stimulators.

As seen in Table 8, the hyper-reactivity of the control BMT+PBS mice against C57Bl stimulator was inhibited following in-vitro treatment with OFF1, similarly to the anergic chimeric BMT+OFF1. Moreover, the responsiveness of both control and chimeric BMT against ICR stimulators was similarly inhibited by in-vitro treatment with OFF1.

TABLE 2

Effect of in-vitro treatment with OFF1: Effect on the immunoresponse of Balb/c mice transplanted with C57Bl Bone marrow.

| | | Bone marrow Recipient | |
| --- | --- | --- | --- |
| Stimulator | In-vitro Treatment | BMT + PBS P.I.[1] | BMT + OFF1 P.I.[1] |
| C57Bl | None | 5.3 | 1.3 |
| | OFF1 | 1 | 1.3 |
| ICR | None | 15.2 | 9.6 |
| | OFF1 | 3.5 | 4.7 |

[1]P.I. Proliferation Index compared with non activated cells (0).

CONCLUSION

Donor marrow treated ex vivo with OFF1 to induce anergy can reconstitute bone marrow with donor chimerism.

Chimeric BMT are anergic to the donor alloantigen but not to other non-related alloantigens, indicating that the chimeric host is not completely immunosuppressed and tolerance is specific. Hyporesponsiveness against additional alloantigens can be further achieved by renewed ex vivo treatment with OFF1 against an additional alloantigen in MLR.

The invention claimed is:

1. An isolated polypeptide consisting of amino acid residues 118 to 165 of SEQ ID NO:5.
2. A composition comprising the polypeptide of claim 1.
3. An isolated DNA molecule encoding the polypeptide of claim 1.
4. The isolated DNA molecule of claim 3 consisting of nucleotides 459 to 602 of SEQ ID NO:1.
5. An expression vector comprising the DNA molecule of claim 3.
6. An isolated host cell transformed with the DNA molecule of claim 3.
7. A method for preparing a polypeptide, comprising:
   culturing the host cell of claim 6 to express a polypeptide consisting of amino acid residues 118 to 165 of SEQ ID NO:5; and
   recovering the expressed polypeptide.
8. A method for treating arthritis, comprising administering to an individual in need thereof the polypeptide of claim 1.

* * * * *